(12) United States Patent
Marchand et al.

(10) Patent No.: US 12,064,345 B2
(45) Date of Patent: Aug. 20, 2024

(54) HEART VALVE ANCHORING DEVICE

(71) Applicant: TRICARES SAS, Paris (FR)

(72) Inventors: Coralie Marchand, Charenton le Pont (FR); Cecile Riou, Paris (FR)

(73) Assignee: TRICARES (SAS), Paris (FR)

( * ) Notice: Subject to any disclaimer, the term of this patent is extended or adjusted under 35 U.S.C. 154(b) by 0 days.

(21) Appl. No.: 17/735,572

(22) Filed: May 3, 2022

(65) Prior Publication Data

US 2022/0257377 A1 Aug. 18, 2022

Related U.S. Application Data

(60) Division of application No. 16/800,404, filed on Feb. 25, 2020, now Pat. No. 11,369,468, which is a (Continued)

(30) Foreign Application Priority Data

Jan. 20, 2014 (EP) .................................... 14151825

(51) Int. Cl.
*A61F 2/24* (2006.01)
(52) U.S. Cl.
CPC .......... *A61F 2/2418* (2013.01); *A61F 2/2436* (2013.01); *A61F 2230/0054* (2013.01); (Continued)
(58) Field of Classification Search
CPC . A61F 2/2418; A61F 2/2436; A61F 2250/006
See application file for complete search history.

(56) References Cited

U.S. PATENT DOCUMENTS

| 5,749,921 A | 5/1998 | Lenker et al. |
|---|---|---|
| 5,840,081 A | 11/1998 | Andersen et al. |

(Continued)

FOREIGN PATENT DOCUMENTS

| EP | 2484309 A1 | 8/2012 |
|---|---|---|
| EP | 3071151 B2 | 7/2017 |

(Continued)

OTHER PUBLICATIONS

European Search Report, EP Application No. 14151825, dated Jun. 3, 2014.

(Continued)

*Primary Examiner* — Suba Ganesan
(74) *Attorney, Agent, or Firm* — The Dobrusin Law Firm, P.C.

(57) ABSTRACT

The present invention relates to an anchoring device (1) designed for anchoring a prosthetic heart valve inside a heart, comprising an extraventricular part (2) designed to be positioned inside an atrium or an artery and a ventricular part (3) designed to be positioned inside a ventricle, wherein the ventricular part comprises a double wall composed of an outer wall (4) and an inner wall (5) spaced apart at the level where the prosthetic heart valve is intended to be inserted, and wherein the anchoring device further comprises a predefined V-shaped groove (8) formed between the extraventricular part (2) and the ventricular part (3). The present invention also relates to an anchoring system (11) for anchoring a prosthetic heart valve inside a heart, comprising said anchoring device (1), a prosthetic heart valve support (12) and a prosthetic heart valve (13) connected to the prosthetic heart valve support (12).

24 Claims, 16 Drawing Sheets

Related U.S. Application Data continuation of application No. 15/492,300, filed on Apr. 20, 2017, now Pat. No. 10,610,355, which is a continuation of application No. 15/112,311, filed as application No. PCT/EP2015/051037 on Jan. 20, 2015, now Pat. No. 10,039,639.

(52) U.S. Cl.
CPC . *A61F 2250/0018* (2013.01); *A61F 2250/006* (2013.01); *A61F 2250/0063* (2013.01); *A61F 2250/0069* (2013.01)

(56) References Cited

U.S. PATENT DOCUMENTS

| | | |
|---|---|---|
| 7,748,389 B2 | 7/2010 | Salahieh et al. |
| 8,070,800 B2 | 12/2011 | Lock et al. |
| 9,782,256 B2 | 10/2017 | Zeng |
| 10,039,639 B2 | 8/2018 | Marchand et al. |
| 10,952,851 B2 | 3/2021 | Marchand |
| 2004/0049207 A1 | 3/2004 | Goldfarb et al. |
| 2004/0186563 A1 | 9/2004 | Lobbi |
| 2005/0137697 A1 | 6/2005 | Salahieh |
| 2006/0020327 A1 | 1/2006 | Lashinski |
| 2006/0271166 A1 | 11/2006 | Thill et al. |
| 2007/0005129 A1 | 1/2007 | Damm et al. |
| 2007/0051620 A1 | 6/2007 | Figulla et al. |
| 2007/0142906 A1 | 6/2007 | Figulla et al. |
| 2007/0244552 A1 | 10/2007 | Salahieh |
| 2007/0270679 A1 | 11/2007 | Nguyen et al. |
| 2008/0071361 A1 | 3/2008 | Tuval et al. |
| 2008/0086107 A1 | 4/2008 | Roschak |
| 2009/0005863 A1 | 1/2009 | Goetz |
| 2009/0054976 A1 | 2/2009 | Tuval et al. |
| 2009/0198315 A1 | 9/2009 | Boudjemline |
| 2009/0222082 A1 | 9/2009 | Lock et al. |
| 2010/0022948 A1 | 1/2010 | Wilson et al. |
| 2010/0256754 A1 | 10/2010 | Styre |
| 2010/0262231 A1 | 10/2010 | Tucal et al. |
| 2010/0292779 A1 | 11/2010 | Straubinger et al. |
| 2011/0029072 A1 | 2/2011 | Gabbay |
| 2011/0046712 A1 | 2/2011 | Melsheimer et al. |
| 2011/0137397 A1* | 6/2011 | Chau .......................... A61F 2/24 623/2.37 |
| 2011/0160836 A1 | 6/2011 | Behen |
| 2011/0208296 A1 | 8/2011 | Duffy et al. |
| 2012/0083874 A1 | 4/2012 | Dale et al. |
| 2012/0101571 A1 | 4/2012 | Thambar et al. |
| 2012/0209122 A1 | 8/2012 | Garbini et al. |
| 2013/0116779 A1 | 5/2013 | Weber |
| 2013/0204357 A1 | 8/2013 | Thill et al. |
| 2013/0274855 A1 | 10/2013 | Stante et al. |
| 2013/0282110 A1 | 10/2013 | Schweich et al. |
| 2013/0304200 A1 | 11/2013 | McLean et al. |
| 2014/0031927 A1* | 1/2014 | Bruchman ............ A61F 2/2415 623/2.18 |
| 2014/0144000 A1 | 5/2014 | Creaven et al. |
| 2014/0155996 A1 | 6/2014 | Wilson et al. |
| 2014/0214157 A1 | 7/2014 | Börtlein et al. |
| 2014/0303719 A1* | 10/2014 | Cox ....................... A61F 2/2466 623/2.37 |
| 2014/0331475 A1 | 11/2014 | Duffy et al. |
| 2014/0350668 A1 | 11/2014 | Delaloye et al. |
| 2015/0005811 A1 | 1/2015 | Lubock et al. |
| 2015/0018938 A1 | 1/2015 | Von Segesser et al. |
| 2015/0045881 A1 | 2/2015 | Lim |
| 2015/0335421 A1 | 11/2015 | Figulla et al. |
| 2015/0335429 A1 | 11/2015 | Morris et al. |
| 2016/0015421 A1 | 1/2016 | Benning et al. |
| 2016/0058976 A1 | 3/2016 | Okamura |
| 2016/0250051 A1 | 9/2016 | Lim et al. |
| 2017/0290661 A1 | 10/2017 | Von Segesser |
| 2018/0049868 A1 | 2/2018 | Board et al. |
| 2018/0325667 A1 | 11/2018 | Gallagher et al. |
| 2019/0046314 A1 | 2/2019 | Levi et al. |
| 2019/0053895 A1 | 2/2019 | Levi |
| 2020/0008941 A1 | 1/2020 | Stappenceck et al. |
| 2020/0121454 A1 | 4/2020 | Spence |
| 2020/0188102 A1 | 6/2020 | Marchand et al. |
| 2020/0360141 A1 | 11/2020 | Stappenceck et al. |
| 2021/0000593 A1 | 1/2021 | Rahmig et al. |

FOREIGN PATENT DOCUMENTS

| | | |
|---|---|---|
| WO | 2001/064137 A1 | 9/2001 |
| WO | 2006/128185 A2 | 11/2006 |
| WO | 2008/118481 A1 | 10/2008 |
| WO | 2009/106545 A1 | 9/2009 |
| WO | 2009/137712 A1 | 11/2009 |
| WO | 2012/178115 A2 | 12/2012 |
| WO | 2013/104721 A1 | 7/2013 |
| WO | 2015/107226 A1 | 7/2015 |
| WO | 2016/090025 A1 | 6/2016 |
| WO | 2017/195125 A1 | 11/2017 |
| WO | 2020/049129 A1 | 3/2020 |
| WO | 2020/127372 A1 | 6/2020 |
| WO | 2020/157018 A1 | 8/2020 |

OTHER PUBLICATIONS

International Search Report, PCT Application No. PCT/EP2015/051037 dated May 6, 2015.

Nkomo, VT. et al., "Burden of valvular heart disease: a population-based study", The Lancet, (2006), vol. 368, pp. 1005-1011.

Mirabel, M. et al., "What are the characteristics of patients with severe, symptomatic, mitral regurgitation who are denied surgery", European Heart Journal, (2007), vol. 28, pp. 1358-1365.

* cited by examiner

HEART VALVE ANCHORING DEVICE

CROSS-REFERENCE TO RELATED APPLICATIONS

This application is a division of U.S. patent application Ser. No. 16/800,404, filed Feb. 25, 2020, which is a continuation of U.S. patent application Ser. No. 15/492,300 filed on Apr. 20, 2017, which is a continuation of U.S. patent application Ser. No. 15/112,311 filed on Jul. 18, 2016, which is a United States national phase application under 35 U.S.C. § 371 of International Application No. PCT/EP2015/051037 filed on Jan. 20, 2015 and claims the benefit of EP Patent Application No. 14151825.8 filed on Jan. 20, 2014, the contents of which are herein incorporated in their entirety by reference. The International Application was published as International Publication No. WO 2015/107226 on Jul. 23, 2015.

FIELD OF INVENTION

The present invention relates to an anchoring device for a heart valve. More particularly the present invention relates to a self-expanding anchoring device designed for implantation of a prosthetic heart valve in a mammalian heart, preferably a human heart.

BACKGROUND OF INVENTION

Valvular heart disease is recognized as a common disease in the elderly population. Prevalence of valvular heart diseases increases indeed with age, from 0.7% in 18-44 year olds to 13.3% in the 75 years and older group (Nkomo, V T. et al., Burden of valvular heart disease: a population-based study, The Lancet, Volume 368, Issue 9540, Pages 1005-1011, 2006).

A mammalian heart valve comprises four heart valves which determine the pathway of blood flow through the heart. A mammalian heart generally comprises two atrioventricular valves namely the mitral valve and the tricuspid valve, which are located between the atria and the ventricles and prevent backflow of blood from the ventricles into the atria; and two semilunar valves (also known as arterioventricular valves) namely the aortic valve and the pulmonary valve, which are located in the arteries leaving the heart and prevent backflow of blood from the arteries into the ventricles.

The mitral valve, also known as the left atrioventricular valve, is composed of two valve leaflets (anterior and posterior), an annulus, a supporting chordae tendinae, and papillary muscles. The tricuspid valve, also known as the right atrioventricular valve, is made up of three valve leaflets (anterior, posterior and septal), an annulus, a supporting chordae tendinae, and papillary muscles. The aortic valve is composed of three valve leaflets (right, left and posterior) and an annulus. The pulmonary valve is made up of three valve leaflets (right, left and anterior) and an annulus. The fibrous aortic annulus, the fibromuscular pulmonary annulus and the muscular tricuspid and mitral annuli are linked to the leaflets. As the heart beats, the leaflets open and close to control the flow of blood. The leaflets of the atrioventricular valves are prevented from prolapsing into the atrium by action of the papillary muscles, connected to the leaflets via the chordae tendinae.

Mitral regurgitation—the mitral leaflets do not close properly leading to abnormal leaking of blood—is the most commonly occurring valve abnormality. In the US, in every age group, mitral regurgitation is the most common valvular disorder with a global prevalence of 1.7%, increasing to 10% in adults above 75 years old. (Nkomo, V T. et al., Burden of valvular heart disease: a population-based study, The Lancet, Volume 368, Issue 9540, Pages 1005-1011, 2006). Besides mitral regurgitation, conditions affecting the proper functioning of the mitral valve also include mitral valves stenosis—the opening of the mitral valve is narrowed leading to systolic function deterioration. Aortic valve, pulmonary valve and tricuspid valve may also be affected by regurgitation and stenosis. Heart valve regurgitation and stenosis have strong humanistic outcomes.

Typically, treatment for heart valve regurgitation or stenosis involves either administration of diuretics and/or vasodilators to reduce the amount of blood flowing back, or surgical procedures for either repair or replacement of the heart valve. Repair approach involves cinching or resecting portions of a dilated annulus, for example by implantation of annular rings which are generally secured to the annulus or surrounding tissue. Alternatively, more invasive procedure involves the replacement of the entire heart valve; mechanical heart valves or biological tissues are implanted into the heart in place of the native heart valve. These invasive procedures are performed either through large open thoracotomies or by percutaneous route.

However, in many repair and replacement procedures, the durability of the devices, or the improper sizing of annuloplasty rings or replacement heart valves, may result in additional issues for the patients. For this reason a significant part of patients with valvular heart diseases are denied for surgery. Indeed, despite guidelines for the management of patients with valvular heart disease, 49% of patients with severe mitral regurgitation, assessed by Doppler-echocardiography, are not referred to for surgery; mainly because of their advanced age, the presence of comorbidities, or impaired left ventricular ejection fraction (Mirabel, M. et al., What are the characteristics of patients with severe, symptomatic, mitral regurgitation who are denied surgery, European Heart Journal, Volume 28, Pages 1358-1365, 2007).

Less invasive approaches recently implemented involve pre-assembled, percutaneous expandable prosthetic heart valves. U.S. Pat. No. 5,840,081 discloses a method for implanting an aortic valve mounted on an expandable stent. However, human anatomical variability makes it difficult to design and size a prosthetic heart valve having the ability to conform to a heart annulus. Especially percutaneous atrioventricular valve replacement is a real challenge as the native atrioventricular valves annuli have a non-circular, non-planar, saddle-like geometry often lacking symmetry.

Technical Issue

According to the Applicant, as a prosthetic heart valve needs a stable and symmetric support during the cardiac cycle to ensure proper functioning, there is a need for devices enabling proper anchoring of prosthetic heart valve within the native heart valve. There is also a continued need to provide a prosthetic heart valve avoiding or preventing trauma to the surrounding tissue and ensuring proper functioning even in case of cardiac valve fibrosis.

Current devices developed for percutaneous heart valve replacement were found unsuitable for the following reasons:

Firstly, many of these existing devices support the prosthetic heart valve while contacting the annulus; thereby directly transferring to the prosthetic heart valve many of the distorting forces exerted by the surrounding tissue and blood as the heart contracts during each cardiac cycle. As cardiac replacement devices further comprise heart valves which require a substantially symmetric, cylindrical support around the prosthetic heart valve for proper opening and closing of the leaflets over years of life, when these devices are subjects to movement and forces from the annulus and other surrounding tissues, the prostheses may be compressed and/or distorted, causing the prosthetic leaflets to malfunction. For example International Patent Application WO 2009/106545 discloses an expandable stent for the positioning and anchoring of valvular prosthesis in an implantation site in the heart of a patient in the treatment of a narrowed cardiac valve (stenosis) or a cardiac valve insufficiency (regurgitation). In this application, the stent comprises at least one fastening portion via which the valvular prosthesis can be connected to the stent. This stent is designed as a single wall structure with a circular section and does not address the issue of geometrical unpredictability. Such device does not really prevent paravalvular leakage. Indeed, as the supporting tissue does not offer a stable circular section, junction between the stent and the native heart valve is not achieved on the entire periphery of the heart valve. Moreover, with a single wall structure the stent does not mechanically isolate the prosthetic heart valve from the surrounding native tissues, thereby preventing proper functioning of the prosthetic heart valve during each cardiac cycle.

Secondly, common stents provide radial anchorage and may migrate or slip relative to the heart wall due to blood flow, movements and forces from the annulus and other surrounding tissues. Some existing devices may overcome this drawback by providing an anchoring device comprising a plurality of hook-shaped elements as disclosed in International Patent Application WO 2001/64137. However, this circular device is inflexible and the seal between the anchoring device and the native heart valve and surrounding tissues is hard to achieve. Furthermore, radial support of the surrounding tissue of an atrioventricular valve is significantly lower than radial support of the surrounding tissue of an aortic valve. Therefore radial anchorage of a stent designed for aortic valve may be insufficient when used for atrioventricular valve replacement.

Thirdly, minimally invasive procedure, without direct vision of the surgical site, strongly relies on cardiac surgeon's skills. The prosthetic heart valve must be able to be maneuvered to the greatest possible extent during implantation procedure so as to ensure optimum positioning accuracy. Misalignment of the anchoring device may indeed lead to leakage and unsealing of the device. International patent application WO 2006/128185 discloses an intravascular cuff, with two mushroom-like ends which, upon deployment, trap the native heart valve. The two ends are released sequentially: in a first step the first end is expanded and may abut against the native heart valve for ensuring proper placement; and in a second step the second end is expanded, thereby completely encasing the native heart valve in the cuff. However, WO 2006/128185 does not disclose a double-wall device at the height of the prosthetic heart valve, but only at the two ends. On a practical point of view, WO 2006/128185 discloses the replacement of the native heart valve in two steps. Firstly, the cuff is released from a first catheter and traps the native heart valve and secondly, an expandable prosthetic heart valve is released from a second catheter inside the lumen of the expanded cuff. Upon expansion of the prosthetic heart valve inside the cuff from the second catheter, the prosthetic heart valve expands the central lumen of the cuff and presses against the native heart valve (cf. [0026] and FIGS. 6 and 7). Consequently, the cuff disclosed by WO 2006/128185 directly transfers the forces exerted by the native heart valve and surrounding tissue to the prosthetic heart valves. Furthermore, the shape of the mushroom-like ends do not closely fits the native surrounding tissue along their entire length.

The present invention addresses and intends to correct the drawbacks of the devices of the prior art. The present invention thus relates to a system for anchoring a prosthetic heart valve inside a heart (hereinafter referred to as the anchoring system) comprising a self-expanding anchoring device (hereinafter referred to as the anchoring device) and a compressible and expandable prosthetic heart valve support—including a prosthetic heart valve—attached to the anchoring device. The anchoring device of the invention comprises: an extraventricular part, a ventricular part comprising a double wall and a predefined V-shaped groove formed between the extraventricular part and the ventricular part. Thus, the anchoring device of the invention (i) provides a geometrical anchorage with both radial sealing and longitudinal support, (ii) prevents direct transfer to the prosthetic heart valve of the forces exerted by the surrounding tissue as the heart contracts during each cardiac cycle and (iii) mechanically isolates the prosthetic heart valve from the surrounding tissue.

SUMMARY

In a first aspect, the invention relates to an anchoring device for anchoring a prosthetic heart valve support supporting a prosthetic heart valve inside a heart, said anchoring device comprising an extraventricular part designed to be positioned inside an atrium or an artery, a ventricular part designed to be positioned inside a ventricle, characterized in that said ventricular part comprises a double wall composed of an outer wall and an inner wall spaced apart at the level where the prosthetic heart valve is intended to be inserted, and further characterized in that the anchoring device comprises a predefined V-shaped groove formed between the extraventricular part and the ventricular part.

In an embodiment, the outer wall and the inner wall are connected at a folded end.

In an embodiment, the extraventricular part comprises at least one extraventricular flange extending from the outer wall or the inner wall.

In an embodiment, the ventricular part comprises a cylindrical inner wall and a substantially conical outer wall having its smaller diameter directed in the direction of the extraventricular part and its larger diameter connected to the cylindrical inner wall at the folded end.

In an embodiment, the inner wall of the ventricular part defines a longitudinal axis and the ventricular side of the groove presents an angle, with regard to the longitudinal axis and in the direction of the ventricular part, ranging from 20° to 80°, and the extraventricular side of the groove presents an angle, with regard to the longitudinal axis and in the direction of the ventricular part, ranging from 65° to 110°.

In an embodiment, the V-shaped groove exhibits an acute angle ranging from 5° to 50°.

In an embodiment, the extraventricular side of the V-shaped groove comprises the at least one extraventricular flange and the ventricular side of the V-shaped groove comprises the outer wall of the ventricular part.

In an embodiment, the anchoring device is designed for anchoring a prosthetic heart valve inside a heart, and comprises an extraventricular part designed to be positioned inside an atrium or an artery, a ventricular part designed to be positioned inside a ventricle, an outer wall and an inner wall, wherein said outer wall and said inner wall are spaced apart at the level where the prosthetic heart valve is intended to be inserted in order to mechanically isolating the inner wall from the outer wall.

In an embodiment, the anchoring device is totally or partially made of a biocompatible alloy such as stainless steel, Nitinol, or cobalt-chromium alloy.

In this embodiment, preferably, outer wall and inner wall are one single piece.

In an embodiment, the outer wall and the inner wall and the inner wall are connected at the end of the ventricular part.

In an embodiment, the anchoring device is made from a flexible braided mesh.

In an embodiment, the anchoring device further comprises a cover covering totally or partially the anchoring device, said cover being preferably made of biological tissue, silicone, polytetrafluoroethylene, polyurethane, polyamide, polyester or mixture thereof.

In an embodiment, the anchoring device further comprises a plurality of arms extending outwardly from the ventricular part in the direction of the extraventricular part for securing the native leaflets.

The invention also relates to an anchoring system for anchoring a prosthetic heart valve inside a heart, comprising an anchoring device as described herein, a prosthetic heart valve support, preferably a self-expanding prosthetic heart valve support, and a prosthetic heart valve connected to the prosthetic heart valve support.

In an embodiment, the prosthetic heart valve support is inserted in the lumen defined by the inner wall of the ventricular part and connected to the inner wall of the ventricular part.

In an embodiment, the anchoring system of the invention is such that the prosthetic heart valve support has higher stiffness than the anchoring device. This embodiment is advantageous in that it may help the outer wall of the anchoring device to fit closely the heart wall around the native heart valve during each cardiac cycle, while the prosthetic heart valve support keeps a stable cross-section ensuring proper functioning of the prosthetic heart valve.

In an embodiment, the anchoring system of the invention is crimped in the lumen of a catheter.

In an embodiment, the anchoring system is be crimped in the lumen of a catheter with the ventricular part located distally in the catheter, the ventricular part and the extraventricular part are released out of the catheter sequentially, and:
  upon release of the ventricular part out of the catheter, the ventricular part expands and provides a mechanical stop which protrudes radially with respect to the catheter and presents an angle of about 90°, with respect to the longitudinal axis of the anchoring device, and then
  upon release of the extraventricular part out of the catheter, the ventricular part returns to its original shape defining a V-shaped groove with the extraventricular part.

In an embodiment, the anchoring system may be crimped in the lumen of a catheter with the extraventricular part located distally in the catheter, the wherein the ventricular part and the extraventricular part, may be released out of the catheter sequentially, and:
  upon release of the extraventricular part out of the catheter, the extraventricular part expands and provides a mechanical stop which protrudes radially with respect to the catheter and presents an angle of about 90°, with respect to the longitudinal axis of the anchoring device, and then
  upon release of the ventricular part out of the catheter, the extraventricular part returns to its original shape defining a V-shaped groove with the ventricular part.

In an embodiment, the anchoring system further comprises a tie which passes through the mesh of the anchoring device enabling the re-introduction of the anchoring system inside a catheter by turning inversely the outer wall once the anchoring system has been totally deployed out of said catheter.

In an embodiment, the anchoring system of the invention further comprises a cover covering totally or partially the prosthetic heart valve support, advantageously the cover is made of biological tissue, silicone, polytetrafluoroethylene, polyurethane, polyamide, polyester or mixture thereof.

In an embodiment, in the anchoring system of the invention the prosthetic heart valve support is made a biocompatible alloy such as stainless steel, Nitinol, or cobalt-chromium alloy.

In an embodiment, the anchoring system further comprises a plurality of arms extending outwardly from the prosthetic heart valve support for securing the native leaflets.

This invention also includes a kit of parts for performing heart valve replacement comprising an anchoring device as described herein, a prosthetic heart valve support, a prosthetic heart valve and optionally a catheter.

Definitions

In the present invention, the following terms have the following meanings:
  As used herein the singular forms "a", "an", and "the" include singular and/or plural reference unless the context clearly dictates otherwise.
  The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value or range within 20 percent, preferably within 10 percent of said given value or range.
  "Anchoring device" refers herein to a self-expanding device designed for allowing the implantation and anchorage of a prosthetic heart valve in a mammalian heart.
  "Anchoring system" refers herein to a system comprising the anchoring device, a prosthetic heart valve support and a prosthetic heart valve.
  With regard to the terms "distal" and "proximal" as used herein, unless otherwise specified, the terms can refer to a relative position of the portions of an anchoring device and/or an associated delivery device with reference to an operator (e.g. a surgeon). For example, referring to a delivery catheter suitable to deliver and position the anchoring device comprising a prosthetic heart valve, "proximal" shall refer to a position closer to the operator of the device or an incision in the human body, and "distal" shall refer to a position that is more distant from the operator of the device or further from the incision.

"Double wall" refers herein to two walls spaced apart in order to mechanically isolating the first wall from the second wall. In the present invention a device with a double wall refers to a double walled device along at least the portion intended to receive the prosthetic heart valve, along the whole ventricular part or along the entire length of the anchoring device.

"Geometrical anchorage" refers herein to the anchorage of the device relative to the entire heart wall from one end to the other end of the anchoring device due to an optimal stress distribution both radially and longitudinally; as seen in FIGS. 4A, 4B and 4C. Within the present invention, the anchoring device pinches the sub- and supra-annular surfaces without applying radial force on the annulus.

"Paravalvular leak or paraprosthetic leak" refers herein to a small opening between the upper and lower part of the native heart valve around the outside of the prosthetic heart valve and/or the outside of the anchoring device.

"Prosthetic heart valve" refers herein to mechanical, biological, textile, elastomeric or tissue-engineered heart valves designed to replicate the function of the natural valves of the human heart.

"Radial anchorage" refers herein to the anchorage of a prosthetic heart wall predominantly by the device radial expansion force.

REFERENCES

Figure 1:
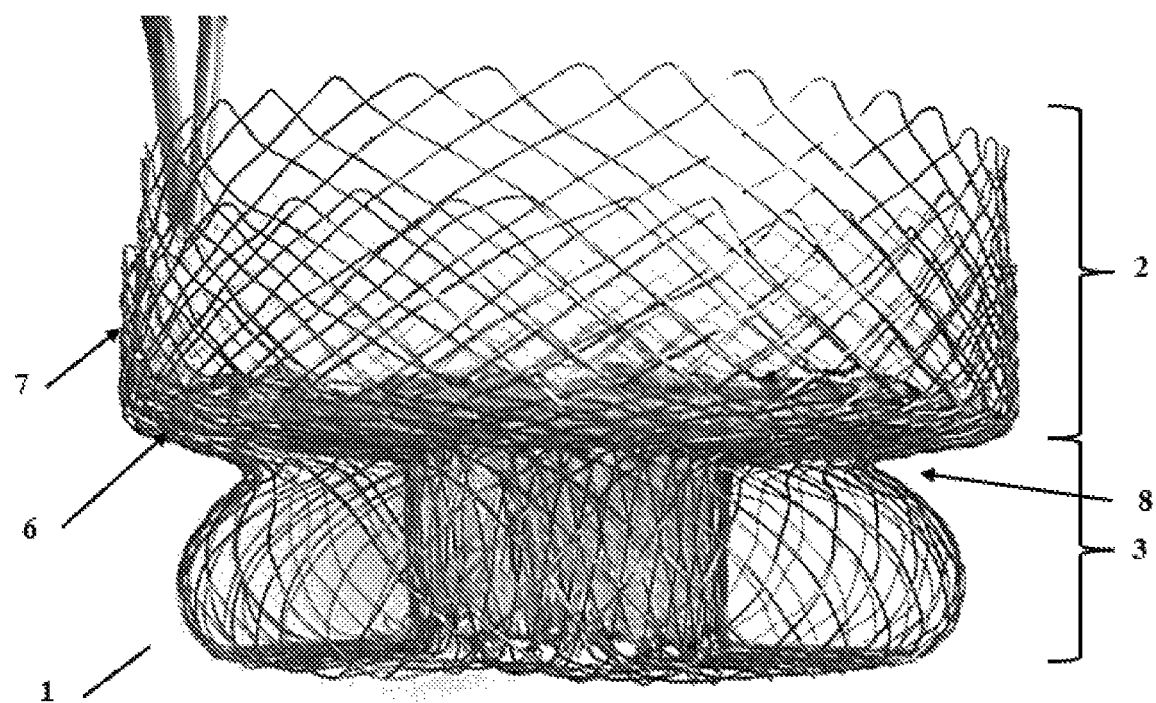
FIG. 1 is a side view of an anchoring device according to an embodiment of the present invention.

1 Anchoring device
2 Extraventricular part of the anchoring device
2d Mechanical stop if the extraventricular part is released in the first step of the deployment
3 Ventricular part of the anchoring device
3d Mechanical stop if the ventricular part is released in the first step of the deployment
4 Outer wall of the anchoring device
5 Inner wall of the anchoring device
6 Flange(s) of the extraventricular part
7 Cylindrical portion(s) of the extraventricular part
8 Groove
9 Cover of the anchoring device
10 Tie
11 Anchoring system
12 Prosthetic heart valve support
13 Prosthetic heart valve
14 Cover of the prosthetic heart valve support
15 Catheter
16 Arms
A Extraventricular area—atrium or artery
V Ventricle

DETAILED DESCRIPTION

The following detailed description will be better understood when read in conjunction with the drawings. For the purpose of illustrating, the anchoring device and the anchoring system are shown in the preferred embodiments. It should be understood, however that the application is not limited to the precise arrangements, structures, features, embodiments, and aspect shown. The drawings are not drawn to scale and are not intended to limit the scope of the claims to the embodiments depicted.

The present invention provides system, device and method to treat heart valve diseases of a mammalian body, preferably a human body.

The present invention relates firstly to an anchoring device designed for implantation of a prosthetic heart valve in a mammalian heart, preferably a human heart.

Referring to the drawings, FIG. 1 illustrates an anchoring device 1 made from a, preferably one single, flexible, compressible and expansible mesh and comprising an extraventricular part 2 and a ventricular part 3. The ventricular part 3 is particularly designed to be positioned inside a ventricle and the extraventricular part 2 is particularly designed to be positioned inside an atrium or inside an artery.

If the anchoring device 1 is designed for anchoring a prosthetic atrioventricular valve, the extraventricular part 2 will be positioned in an atrium. If the anchoring device 1 is designed for anchoring a prosthetic semilunar valve, the extraventricular part 2 will be positioned in an artery.

The anchoring device 1 is of general cylindrical shape.

The anchoring device 1 is a double-walled device. In an embodiment, the anchoring device 1 comprises an outer wall 4 and an inner wall 5. In an embodiment, the inner wall 5 and the outer wall 4 are connected at a folded end and form a single piece.

In an embodiment, the anchoring device 1 is made from a single mesh, forming a general cylindrical shape, folded at one end (the folded end) and extending back up to form an outer wall 4 close and parallel, but spaced, from the inner original wall 5, said outer wall finishing as a cylindrical rim.

According to one embodiment, as detailed hereafter, the inner wall 5 and the outer wall 4 are connected only at the single folded end. In an embodiment, the outer wall 4 and the inner wall 5 are connected at the bottom of the ventricular part 3.

In an embodiment, the anchoring device 1 presents a double wall along the whole height of the device 1. In an embodiment, the anchoring device 1 presents a double wall along the whole height of the device 1 except at the non-folded end. In an embodiment, the anchoring device 1 presents a double wall at the height of the native heart valve, especially at the height of the annulus of the native heart valve. In an embodiment, the anchoring device 1 presents a double wall along the ventricular part 3.

Figure 2:
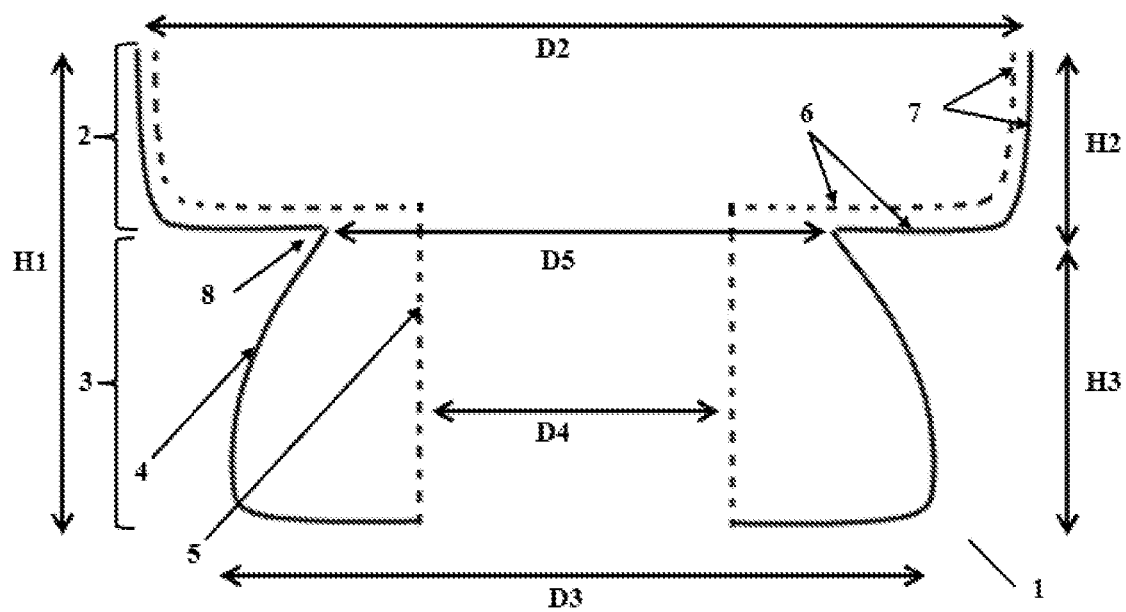
FIG. 2 is a sectional drawing of the anchoring device according to an embodiment of the present invention.
Figure 11:
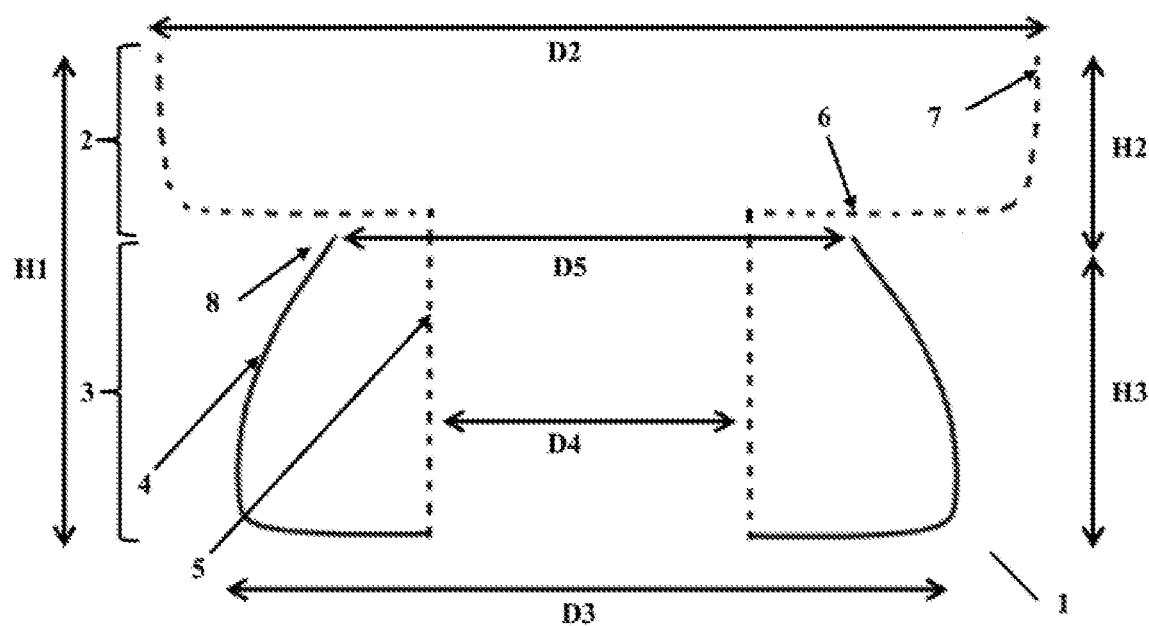
FIG. 11 is a sectional drawing of the anchoring device according to an embodiment of the present invention.

In an embodiment, the inner wall 5 is spaced apart from the outer wall 4 so that the inner wall 5 is mechanically isolated with respect to the surrounding tissues. In an embodiment, the outer wall 4 and the inner wall 5 are spaced apart, at least at the level where the prosthetic heart valve is intended to be inserted in order to mechanically isolating the inner wall 5 from the outer wall 4. In an embodiment, the outer wall 4 and the inner wall 5 are spaced apart at the height of the native heart valve, especially at the height of the annulus of the native heart valve. In an embodiment, the outer wall 4 and the inner wall 5 are spaced apart along the ventricular part 3. In an embodiment, the outer wall 4 supports the major part of the stresses from the surrounding tissues and the inner wall 5 exhibits a stable cross-section whatever the forces exerted by the surrounding tissue. Referring to FIGS. 2 and 11, illustrating a cross sectional view of the anchoring device 1, the outer wall 4 is shown in full line and the inner wall 5 is shown in dotted line. In an embodiment, the outer wall 4 and the inner wall 5 have the same stiffness. In an alternative embodiment, the outer wall 4 exhibits lower stiffness than that of the inner wall 5.

According to the invention, the device comprises a groove or a recess 8, designed for accommodating the native heart valve, especially the annulus of the native heart valve. In an embodiment, the groove 8 is at the junction between the extraventricular part 2 and the ventricular part 3. In an embodiment, the groove 8 is formed between the extraventricular part 2 and the ventricular part 3. In a preferred embodiment, the groove 8 is V-shaped.

In an embodiment, the groove 8 is designed to accommodate, pinch, contain and press the native heart valve, especially the annulus of the native heart valve. In an embodiment, the groove 8 has a depth ranging from 1 to 30 millimeters, preferably from 5 to 15 millimeters, more preferably from 5 to 10 millimeters. As explained thoroughly hereafter, it is an object of the groove 8 of the invention to position the anchoring device with respect to the native heart valve due to sub- and supra-annulus anchoring without radial anchoring at the height of the annulus; thereby avoiding trauma. In a preferred embodiment, the extraventricular part 2, the groove 8 and the ventricular part 3 are integral and formed in a single piece.

In an embodiment, the extraventricular part 2 of the anchoring device 1 comprises at least one extraventricular flange 6 extending from the outer wall 4 and/or from the inner wall 5. In an embodiment, the extraventricular part 2 of the anchoring device 1 comprises two extraventricular flanges 6 extending from the outer wall 4 and from the inner wall 5.

In an embodiment, the at least one extraventricular flange 6 forms the extraventricular side of the groove 8.

In an embodiment, the extraventricular part 2 of the anchoring device 1 comprises at least one cylindrical portion 7 extending from the at least one extraventricular flange 6 in the direction opposite to the ventricular part. In an embodiment, the extraventricular part 2 of the anchoring device 1 comprises two cylindrical portions 7 extending from each of the two extraventricular flanges 6.

In the embodiment depicted in FIGS. 1 and 2, the extraventricular part 2 of the anchoring device 1 comprises two extraventricular flanges 6 extending, one from the inner wall 5, and the other one from outer wall 4, and two cylindrical portions 7 extending from each of said extraventricular flanges 6 in the direction opposite to the ventricular part 3.

In an embodiment, the extraventricular flange of the inner wall 5 is folded into itself and the rim of said extraventricular flange is inserted between the outer wall 4 and the inner wall 5 of the ventricular part 3. Thus the extraventricular flange 6 of the inner wall 5 is located in the ventricular part 3.

Figure 10:
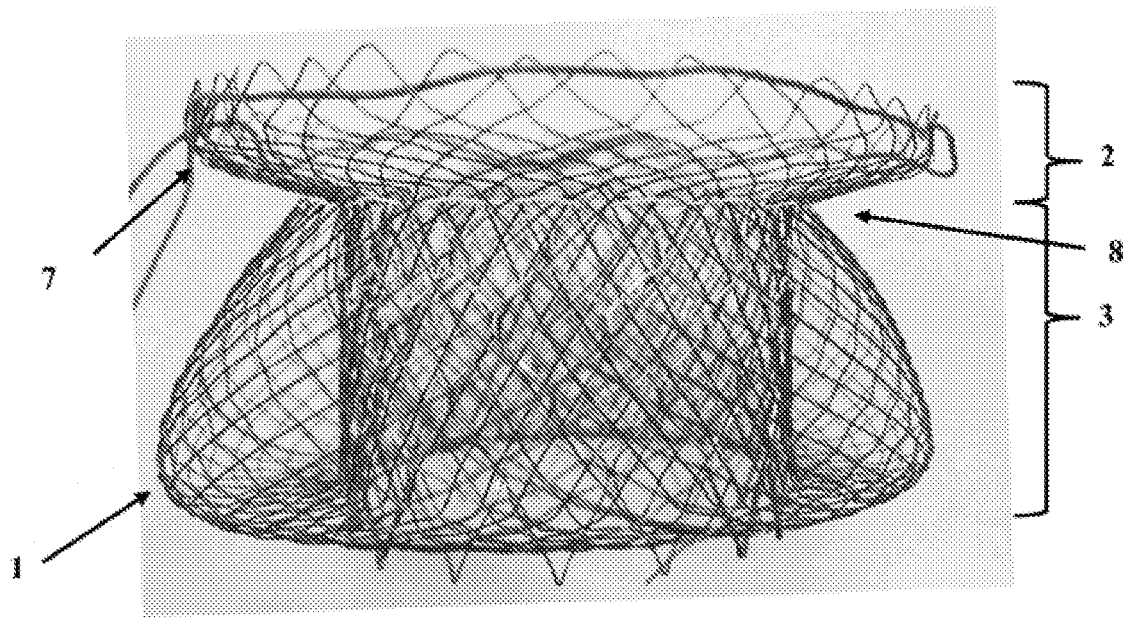
FIG. 10 is a side view of an anchoring device according to an embodiment of the present invention.

In another embodiment depicted in FIGS. 10 and 11, the anchoring device 1 comprises only a single extraventricular flange 6 which extends from the inner wall 5. The rim of the outer wall 4 of the ventricular part 3 is free and not connected to the extraventricular flange 6.

According to an alternative embodiment, not shown, the rim (i.e. the non-folded end) of the outer wall 4 is connected to the extraventricular flange 6 by any means that one skilled in the art would find suitable such as for example suture or mesh interlacing. In an embodiment, the outer wall 4 of the ventricular part 3 is connected to the extraventricular flange 6 along a circle having a diameter ranging between D2 and D4.

In an embodiment, the extraventricular flange(s) 6 extends radially with respect to the longitudinal axis of the anchoring device 1. In an embodiment, the extraventricular flange(s) 6 extends with an angle, with respect to the longitudinal axis and in the direction of the ventricular part 3, ranging from 65° to 110°, preferably from 75° to 100°, more preferably from 85 to 105°. In an embodiment, the outer wall 4 of the ventricular part 3 extends with an angle, with respect to the longitudinal axis and in the direction of the ventricular part 3, ranging from 20° to 80°, preferably from 30° to 60°, more preferably from 40 to 50°.

The extraventricular flange(s) 6 may be constructed of different geometric shapes, such as circular, oval, star, petal, or ratchet. The extraventricular flange(s) 6 may take on different profiles, when viewed from its side. In one embodiment, the profile of the extraventricular flange(s) 6 is curved or ridged. The different geometric shapes and profiles of the extraventricular flange(s) 6 provide better contact, stability and grip between the extraventricular flange(s) 6 and the extraventricular side of the native annulus. The extraventricular flange(s) 6 are configured for positioning substantially flat against the extraventricular side of the native annulus to prevent migration of the anchoring device 1 in at least one direction following implantation. For instance, if the anchoring device 1 is designed for anchoring a prosthetic mitral valve or prosthetic tricuspid valve, the at least one extraventricular flange 6 is configured to anchor the extraventricular side (i.e. the atrial side) of the mitral annulus, respectively the tricuspid annulus.

In one embodiment, the cylindrical portions 7 is replaced by a folded portion, a rounded portion, a conic portion, a cylinder having a diameter of about D2, or a mixture thereof.

In an embodiment, the extraventricular flanges 6 of the outer wall 4 and of the inner wall 5 of the extraventricular part 2 are extended in the direction opposite to the ventricular part 3 by cylindrical portions 7 having a diameter of about D2. Without portion 7, the outer end of the mesh of the extraventricular flanges 6 may perforate the atrial or arterial wall. Use of a portion(s), preferably a cylindrical portion(s) 7, extending from the extraventricular flange(s) 6 in the direction opposite to the ventricular part 3 limits the risks of puncture of the atrial or arterial wall and provides an atraumatic extraventricular part 2. In an embodiment, the inner portion 7 has a height higher than the outer portion 7. In an embodiment, the inner wall 5 of the extraventricular part 2 has a height higher than the height of the outer wall 4 of the extraventricular part 2. In said embodiment, the inner wall 5 of the extraventricular part 2 is higher from 2 to 15 millimeters, preferably from 3 to 10 millimeters with respect to the outer wall 4 of the extraventricular part 2. In an embodiment, the inner wall 5 of the extraventricular part 2 and the outer wall 4 of the extraventricular part 2 have the same height. In an embodiment, the outer portion 7 has a height higher than the inner portion 7. In an embodiment, the outer wall 4 of the extraventricular part 2 has a height higher than the height of the inner wall 5 of the extraventricular part 2.

In an embodiment, the inner wall 5 and the outer wall 4 are spaced apart, except at the height of the extraventricular flanges 6 and the cylindrical portions 7 and at the folded end.

In one embodiment, the extraventricular flanges 6 have the shape of an annulus, the outer circle having a diameter equal to about D2 and the inner circle having a diameter equal to about D4 for the extraventricular flange 6 extending from the inner wall 5, and equal to about D5 for the extraventricular flange 6 extending from the outer wall 4. In an embodiment, said two extraventricular flanges have different outer diameters.

The inner wall 5 of the ventricular part 3 has a cylindrical cross section with a diameter equal to about D4. The outer wall 4 of the ventricular part 3 has an approximately toroidal shape. In a preferred embodiment, the outer wall 4 of the ventricular part 3 has an approximately conical shape whose smaller diameter is directed in the direction of the extraventricular part 2. In an embodiment, the outer wall 4 of the ventricular part 3 has the shape of a conical body which slopes inwardly in the direction of the extraventricular part 2. In an embodiment, the end of the ventricular part 3, close to the groove 8 and to the extraventricular part 2, has a smaller cross-sectional area than the folded end of the ventricular part 3.

In an embodiment, the junction between the approximately toroidal part of the outer wall 4 of the ventricular part and the at least one extraventricular flange 6 of the outer wall 4 or inner wall 5 defines a V-shaped groove 8. Said V-shaped groove 8 allows pinching or cinching of the native heart valve, especially of the annulus of the native heart valve throughout the cardiac cycle. In an embodiment, a V-shaped groove 8 is formed between the extraventricular flange 6 and the outer wall 4 of the ventricular part 3.

The V-shaped groove 8 has a first extraventricular side (the extraventricular flange 6 of the inner wall 5 or the outer wall 4) extending with an angle, with respect to the longitudinal axis and in the direction of the ventricular part, ranging from 65° to 110°, preferably from 75° to 100°, more preferably from 85 to 105°. The V-shaped groove 8 has a second ventricular side (the outer wall 4 of the ventricular part 3) extending with an angle, with respect to the longitudinal axis and in the direction of the ventricular part, ranging from 20° to 80°, preferably from 30° to 60°, more preferably from 40 to 50°. The longitudinal axis is defined as the longitudinal axis of the inner wall 5 of the ventricular part 3. Said V-shaped groove 8 allows easy positioning of the native heart valve, preferably of the annulus of the native heart valve, inside said groove 8. In an embodiment, the V-shaped groove exhibits an acute angle between the edges of the groove. In an embodiment, the V-shaped groove 8 exhibits an angle ranging from 5° to 50°, preferably ranging from 10° to 30°.

In an embodiment, the anchoring device 1, and especially the groove 8, enables anchorage at a native heart valve location by engagement with sub-annular and super-annular surfaces of the heart valve annulus and/or valve leaflets. In an embodiment, the V-shaped groove 8 has a depth ranging from 1 to 30 millimeters, preferably from 5 to 15 millimeters, more preferably from 5 to 10 millimeters. In an embodiment, the V-shaped groove 8 enables self-positioning of the anchoring device 1. Indeed the V-shaped groove 8 is positioned by itself with the bottom of the V-shaped groove 8 in the plane defined by the valvular annulus due to the two inclined sides of the groove 8. Thus the anchoring device 1 is precisely positioned with respect to the native heart valve anatomy while other devices without groove or with U-shaped, C-shaped or rounded-bottom grooves do not provide such precision and self-positioning. The V-shaped groove 8 of the present invention also prevents any migration of the anchoring device 1 with respect to the valvular annulus. Furthermore, the V-shaped groove 8 enables to anchor the anchoring device with the sub- and supra-annulus surface. The annulus does not contact the bottom of the V-shape groove thus avoiding radial compression of the annulus.

In an embodiment, the anchoring device 1, and especially the groove 8, the extraventricular flange(s) 6 and the outer wall 4 of the ventricular part 3 do not only catch or trap the leaflets of the native heart valve but also presses said leaflets against, or at least in the direction of, the heart wall. In an embodiment, the anchoring device 1 has the flexibility to adapt and conform to the variably-shaped native heart valve anatomy while mechanically isolating the prosthetic heart valve. The outer wall 4 is indeed in close contact with the atrial or arterial wall, with the ventricular wall, and with the native heart valve and annulus; while the inner wall 5 is mechanically isolated due to the double wall and the low stiffness of the anchoring device 1. In an embodiment, the inner wall 5 of the ventricular part 3 has a stable cross section with a diameter equal to about D4, for receiving the prosthetic heart valve.

According to one embodiment, the outer wall 4 spaced from the inner wall 5 at the height of the prosthetic heart valve enables proper functioning of prosthetic heart valve even in case of valve fibrosis. Valve fibrosis refers to abnormal thickening of the heart valve. In the event of valve replacement the native leaflets of the replaced valve do not open and close regularly thereby leading to thickening and fibrosis. Said fibrosis and thickening prevent optimal functioning of standard prosthetic heart valve. Due to the double wall of the present invention, the prosthetic heart valve of the present invention is not obstructed by the thickened leaflets. The outer wall 4 maintains indeed advantageously the valvular apparatus against or in the direction of the heart wall, away from the inner wall 5 and the prosthetic heart valve.

In an embodiment, a U-shaped groove 8 is formed between the extraventricular flange 6 and the outer wall 4 of the ventricular part 3.

Figure 12:
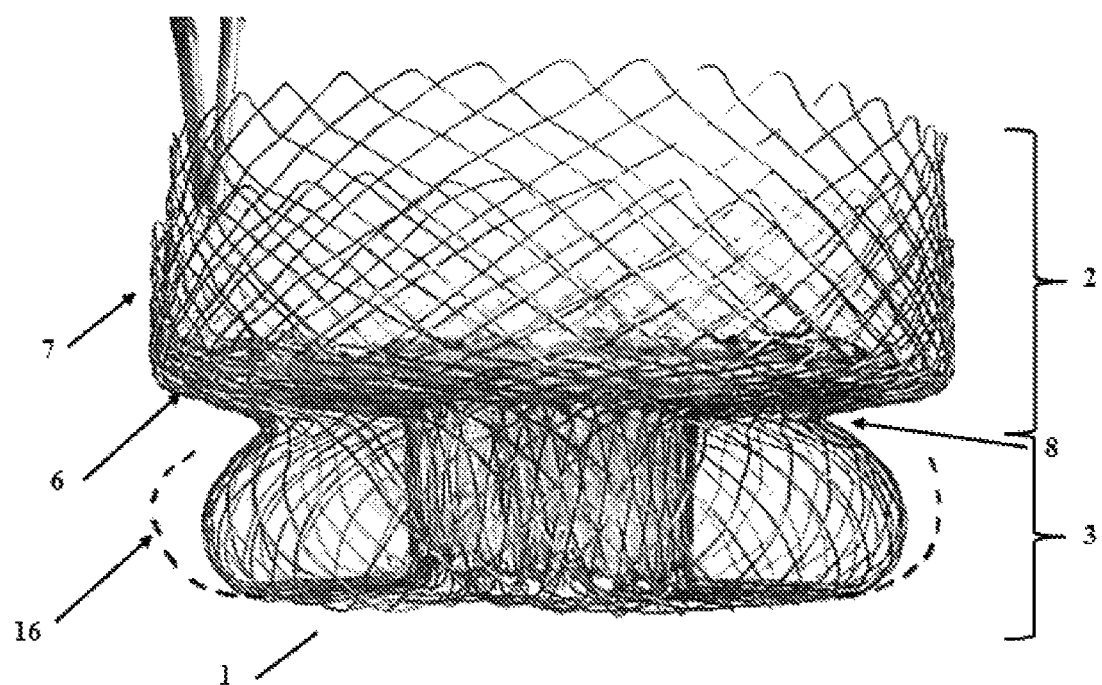
FIG. 12 is a side view of an anchoring device according to an embodiment of the present invention wherein the anchoring device comprises a plurality of arms extending outwardly from the ventricular part.

According to one embodiment, as depicted in FIG. 12, the anchoring device 1 further comprises a plurality of arms 16 for securing the device with respect to the native heart valve. The plurality of arms 16 extends outwardly from the ventricular part 3, preferably from the outer wall 4 of the ventricular part 3. According to one embodiment, the plurality of arms extends outwardly from the folded end of the ventricular part 3 in the direction of the extraventricular part 2. Said plurality of arms 16 are configured to be size and shape for providing a positioning and anchoring function when the anchoring device 1 is deployed at the native heart valve location.

In one embodiment, the plurality of arms 16 has a length sufficient to extend completely into engagement with the annulus tissue behind the leaflets. According to one embodiment, the plurality of arms 16 comprises arms with various lengths and thereby various modes of engagement with the leaflets or other native tissue.

The plurality of arms 16 may alternatively be configured to engage or couple to the chordae, papillary muscles, leaflets or ventricular walls to enhance anchoring. In one embodiment, each arms of the plurality of arms 16 have independent lengths. In one embodiment, the native leaflets are pinched or sandwiched between the plurality of arms 16 and the outer wall 4.

According to one embodiment, the plurality of arms 16 is formed integrally with the ventricular part 3, especially with outer wall 4 of the ventricular part 3. According to another embodiment, the plurality of arms 16 is separate component that are attached to the ventricular part 3. According to one embodiment, the plurality of arms 16 is made from the same material than the outer wall 4 of the anchoring device 1.

According to an embodiment (not depicted), the anchoring device 1 also comprises a grabbing mechanism on the outer wall 4, preferably on the outer wall 4 of the ventricular part 3. In an embodiment, the grabbing mechanism comprises a plurality of projections, preferably anchors, hooks or barbed projections. Said grabbing mechanism at least partially penetrates and engages the surrounding tissue and preferably the native leaflets. In one embodiment, the grabbing mechanism is positioned outwardly on the outer wall 4, preferably on the outer wall 4 of the ventricular part 3, for instance in one or more horizontal or circumferential strips. Preferably the grabbing mechanism is located on the outer wall 4 of the ventricular part 3 in the V-shaped groove 8. According to one embodiment, the projections may have different lengths. According to one embodiment, the grabbing mechanism projects outwardly from 1 to 3 millimeters from the outer wall, preferably from 1 to 2 millimeters. According to one embodiment, the grabbing mechanism is oriented towards the extraventricular part 2. According to one embodiment, the grabbing mechanism is made from the same material than the outer wall 4 of the anchoring device 1.

The combination in an embodiment of the anchoring device 1 of the present invention of the double wall (i.e. the outer wall 4 and the inner wall 5 spaced apart but connected at a folded end and the V-shaped groove 8) with the plurality of arms 16 and/or the grabbing mechanism enables maintaining and containing the valvular apparatus and especially the native leaflets in a fixed position; thereby ensuring proper functioning of the prosthetic heart valve to be inserted in the anchoring device. Indeed the anchoring device 1 advantageously contains and maintains the native leaflets due to the combination of:

- the double wall, maintaining the native leaflets in the direction of the heart wall, away from the prosthetic valve;
- the plurality of arms 16 and/or the grabbing mechanism fixedly maintaining and containing the native leaflet with respect to the anchoring device 1, preventing undesirable movement; and
- the plurality of arms 16, and/or the grabbing mechanism, and the V-shaped groove 8 maintaining and containing the native leaflets and strongly anchoring the device 1 at the desired location.

Again referring to FIG. 2, D2 refers to the external diameter of the extraventricular part 2; D3 refers to the largest external diameter of the ventricular part 3; D4 refers to the internal diameter of the ventricular part 3; D5 refers to the smallest external diameter of the ventricular part or equally to the external diameter at the height of the groove 8. H1 refers to the height of the whole anchoring device 1; H2 refers to the height of the extraventricular part 2, preferably of the height of the outer wall 4 of the extraventricular part 2; and H3 refers to the height of the ventricular part 3. Said diameters and heights refer to the diameters and heights of the anchoring device 1 at the time of manufacture.

In an embodiment, D2 ranges from 10 to 90 millimeters, preferably from 20 to 85 millimeters, more preferably from 30 to 70 millimeters.

In an embodiment, D3 ranges from 10 to 90 millimeters, preferably from 20 to 80 millimeters, more preferably from 30 to 70 millimeters. In a preferred embodiment, D2 is equal or higher than D3.

In an embodiment, D4 ranges from 5 to 40 millimeters, preferably from 10 to 30 millimeters, more preferably from 15 to 25 millimeters.

In an embodiment, D5 ranges from 10 to 75 millimeters, preferably from 20 to 70 millimeters, more preferably from 30 to 65 millimeters, even more preferably about 35 millimeters.

In an embodiment, H1 ranges from 5 to 50 millimeters, preferably from 10 to 40 millimeters, more preferably from 20 to 30 millimeters, even more preferably about 25 millimeters.

In an embodiment, H2 ranges from 1 to 20 millimeters, preferably from 3 to 15 millimeters, more preferably from 5 to 10 millimeters.

In an embodiment, H3 ranges from 1 to 45 millimeters, preferably from 5 to 35 millimeters, more preferably from 10 to 25 millimeters, even more preferably about 15 millimeters.

In an embodiment, the mesh of the anchoring device 1 is a braided mesh, preferably a flexible braided mesh. Said braided mesh allows lower stiffness, minimal stress, higher conformability and higher deformability than continuous mesh. Braiding offers good compressibility, enhances the conformation with the heart wall and prevents paravalvular leaks. In an embodiment, the mesh of the anchoring device 1 may be braided from one or more strands, preferably one strand. In another embodiment, the mesh of the anchoring device 1 may be a continuous mesh obtained by any means that a person skilled in the art would find suitable, such as, for example, laser cutting.

In an embodiment, the mesh of the anchoring device 1 is thermoformed in order to provide the double wall anchoring device 1 of the present invention. Said heat treatment uses common technical knowledge known by a person with ordinary skill in the art, such as for example thermoforming on a heated metal mandrel. During thermoforming, the mesh is reverted (i.e. folded into itself), thus forming in a single piece an inner wall 5 connected at a folded end with an outer wall 4.

In an embodiment, the mesh of the anchoring device 1 is compressible and has a radially collapsed configuration for delivery through a catheter and a radially expanded configuration for deployment.

In an embodiment, the anchoring device 1 keeps its structure (i.e. a double wall, an extraventricular part, a V-shaped groove and a ventricular part) before crimping and insertion in the catheter and during use. In an embodiment, the anchoring device 1 is not folded into itself between the delivery configuration and the expanded configuration. In an embodiment, the anchoring device 1 is already folded into itself in the delivery configuration. In an embodiment, the anchoring device comprises before use an outer wall 4 and an inner wall 5 connected at a folded end. In an embodiment, the V-shaped groove 8 is preconfigured or predefined, i.e. the anchoring device 1 already exhibits its V-shaped groove 8 before crimping in the delivery catheter.

In an embodiment, the anchoring device 1 is made from any material that one skilled on that art would find suitable, such as any biocompatible material. In an embodiment, the anchoring device 1 is made from any biocompatible alloy that one skilled in the art would find suitable such as for example a cobalt alloy, preferably a cobalt-chromium alloy; steel, preferably stainless steel; or a biocompatible shape memory alloy. In an embodiment, the anchoring device 1 is made from a shape memory alloy, preferably Nitinol, allowing faster and easier deployment and return to its original expanded shape. In an embodiment, the anchoring device is made from Nitinol due to its superelastic and shape-memory features. In an embodiment, the transformation temperature of the shape memory alloy, preferably Nitinol, ranges from 0° C. to 50° C. In an embodiment, the transformation temperature of the shape memory alloy is about 37° C. In another embodiment, the transformation temperature of the shape memory alloy, preferably nitinol, ranges from 0° C. to 20° C. in order to allow phase transformation immediately from the releasing of the anchoring device 1 in the human body.

Figure 3A:
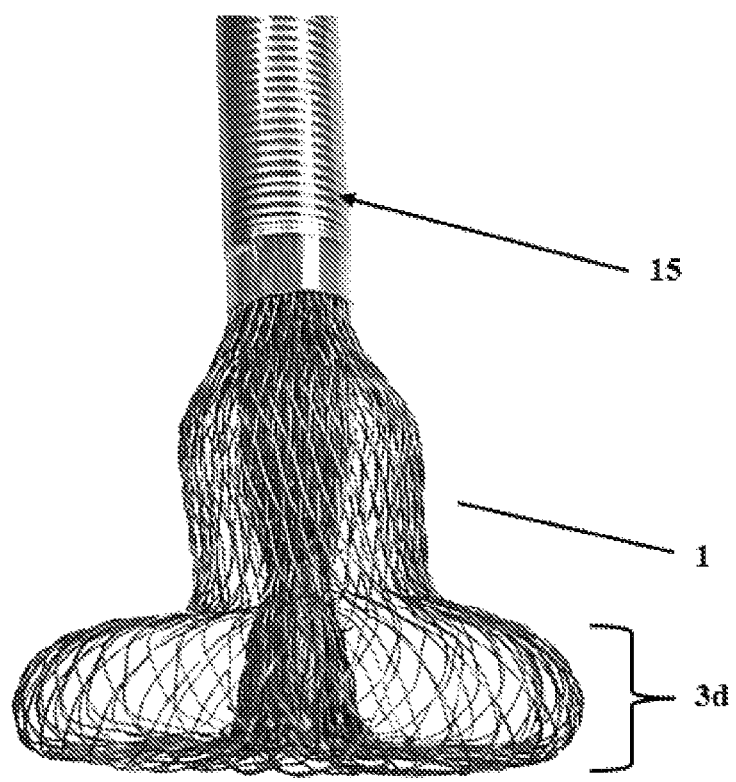
FIGS. 3A, 3B and 3C are side views of an anchoring device during deployment out of a catheter according to an embodiment of the present invention.
Figure 3B:
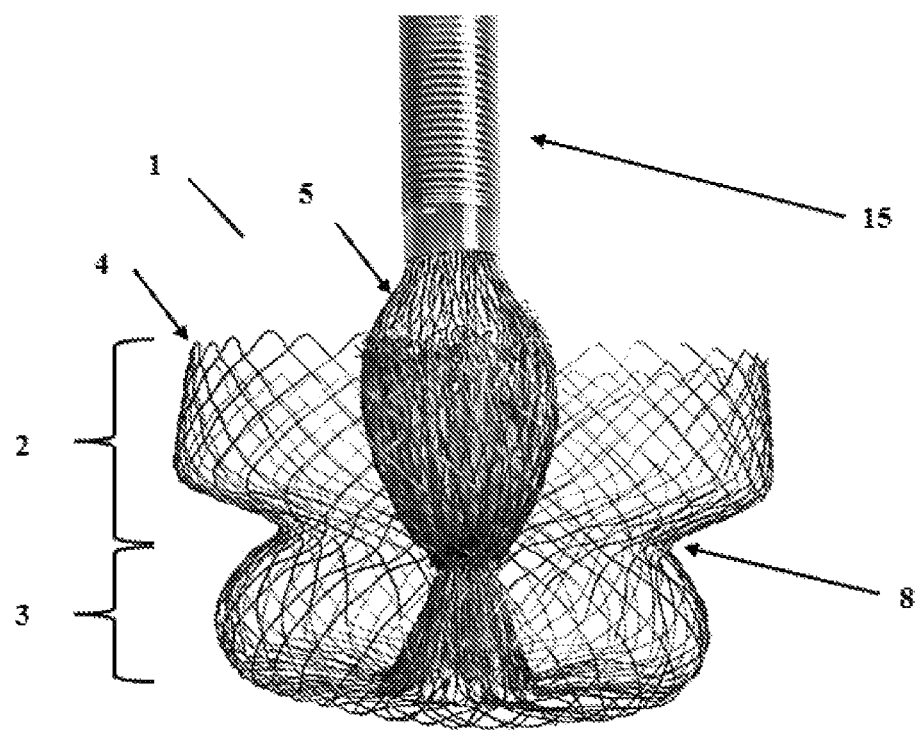
Figure 3C:
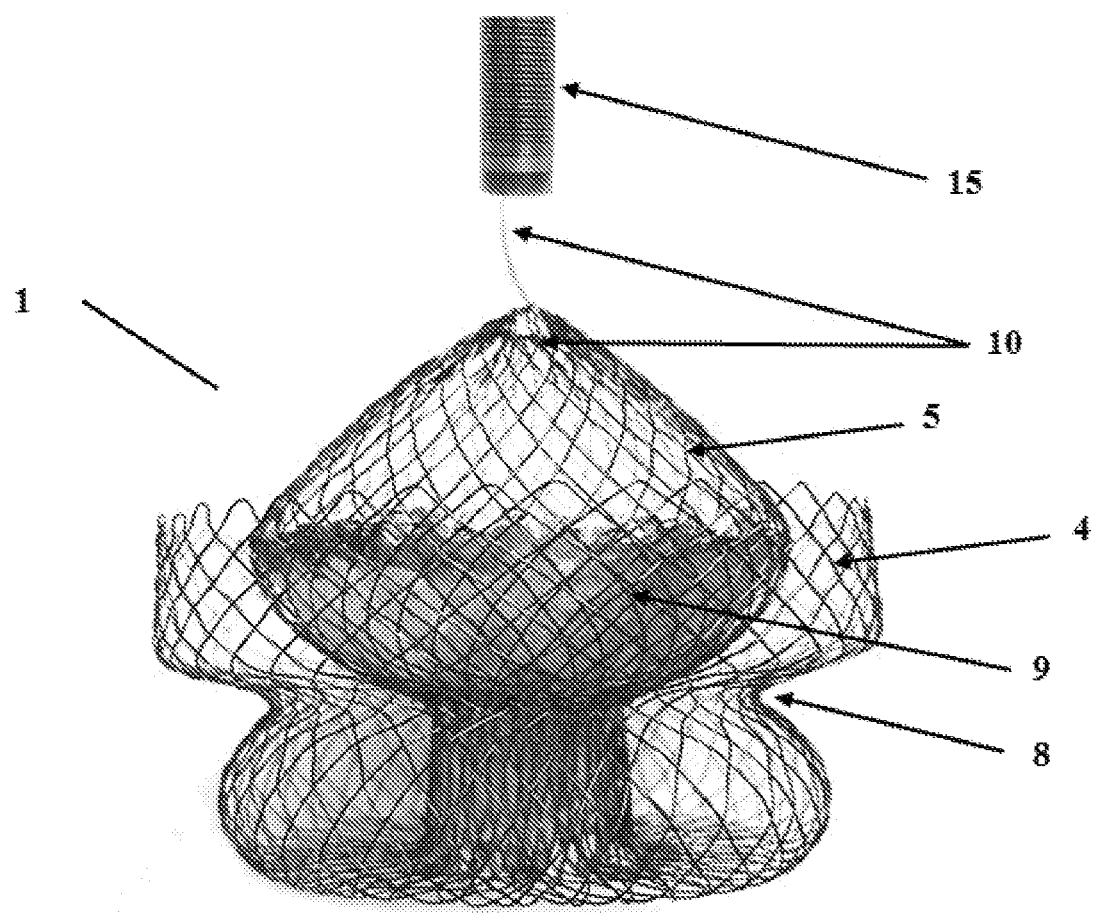

In an embodiment, as illustrated in FIG. 3C, the anchoring device 1 further comprises a cover 9. In an embodiment, the anchoring device 1 comprises a cover 9 covering the anchoring device 1. In an embodiment, the cover 9 partially or totally covers the anchoring device 1. In a first embodiment, the cover 9 internally or externally covers the outer wall 4 of the anchoring device 1. In a second embodiment, the cover 9 internally or externally covers the inner wall 5 of the anchoring device 1. In preferred embodiment, said cover 9 is watertight and thus prevents paravalvular or paraprosthetic leakage through the anchoring device 1. In a preferred embodiment, the cover 9 internally or externally covers the inner wall 5; more preferably internally covers the inner wall 5 of the anchoring device 1. In a preferred embodiment, as disclosed in FIG. 7B, the cover 9 covers the extraventricular flange 6 of the inner wall 5 of the extraventricular part 2 and the entire inner wall 5 of the ventricular part 3. In the embodiment of FIG. 3C, the outer wall 4 is uncovered thus allowing ingrowth and interpenetration between the mesh of the outer wall 4 and the heart wall, enhancing the anchorage.

In an embodiment, as disclosed in FIG. 3C, the anchoring device 1 comprises a tie or a suture 10 releasably linking the anchoring device 1 to a catheter 15. In an embodiment, the anchoring device 1 comprises a tie 10 extending through some or all of the meshes of the inner wall 5, preferably passing through some or all of the meshes of the rim of the extraventricular flange 6 of the inner wall 5. In an embodiment, the tie 10 passes through at least 50% of the meshes of the rim of the extraventricular flange 6 of the inner wall 5. In an embodiment, the anchoring device 1 comprises a tie 10 passing through some or all of the meshes of the outer wall 4, preferably passing through some or all of the meshes of the folded end of the outer wall 4. In an embodiment, the tie 10 passes through at least 50% of the meshes of the folded end of the outer wall 4. In an embodiment, the tie 10 may slide through the mesh. In an embodiment, the tie 10 is made from a resorptive suture strand. In an embodiment, the tie 10 is made from a non-resorptive suture strand. Said tie 10 is useful for the removal of the anchoring device by re-introduction of the anchoring device 1 inside a catheter 15 during implantation of the anchoring device as explained hereafter.

The present invention also relates to a method of delivery and implantation of an anchoring device designed to anchor a prosthetic heart valve inside a native heart valve.

The present method advantageously enables self-positioning of the anchoring device 1 due to the V-shaped groove 8. In particular the V-shaped groove 8 ensures self-positioning of the anchoring device 1 by positioning the bottom of the V-shaped groove 8 in the plane defined by the valvular annulus due to the two inclined sides of the groove 8.

Referring now to FIGS. 3A, 3B and 3C and to FIGS. 6A, 6B, 6C and 6D, the deployment of the anchoring device 1 is illustrated. As well-known from one skilled in the art, the anchoring device 1 is initially crimped and introduced inside the lumen of a catheter 15. In a preferred embodiment, the anchoring device 1 is crimped with a cold-working technique. The assembly of the anchoring device 1 inside a catheter 15 is well known by a person with ordinary skill in the art.

A small incision is achieved to expose a body channel—e.g. an artery or a vein- or the apex of the heart, through which the insertion of the catheter 15 takes place. The catheter 15 is advanced until the distal end of the catheter 15 crosses the targeted native heart valve. Once the distal part of the catheter 15 crossed the annulus of the native heart valve, the anchoring device 1 may be released progressively and sequentially. Depending of the heart valve to be replaced, various surgical approaches may be implemented such as for example retrograde trans-femoral approach or antegrade trans-apical approach for replacement of an aortic valve, retrograde trans-apical approach for replacement of a mitral valve, antegrade jugular approach for the replacement of a tricuspid valve. Depending of the surgical approach, the distal part of the catheter may be located (i) in a ventricle or (ii) in an atrium or an artery. Depending of the surgical approach and the heart valve to be treated, the anchoring device 1 may be inserted into the lumen of the catheter 15 with either (i) the ventricular part 3 located distally (i.e. at the distal end of the catheter) and the extraventricular part 2 located proximally, or (ii) the extraventricular part 2 located distally (i.e. at the distal end of the catheter) and the ventricular part 3 located proximally.

Figure 8:
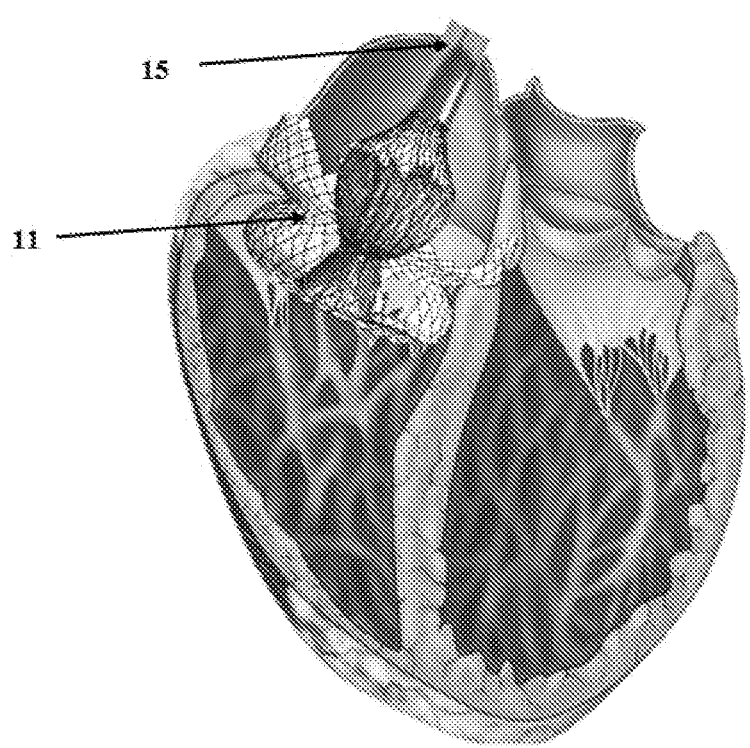
FIG. 8 is a sectional view, illustrating the positioning in a human heart of the anchoring system according to one embodiment of the present invention, wherein the deployment has been implemented sequentially with first release of the ventricular part and then release extraventricular part.

The following description is related to the deployment of the anchoring device 1 out of a catheter 15, wherein the distal end of the catheter 15 is located in a ventricle before the beginning of the deployment (cf. FIG. 8). The ventricular part 3 is thus located distally and the extraventricular part 2 is located proximally within the lumen of the catheter 15. Said deployment is illustrated in FIGS. 3A, 3B and 3C.

Once the distal end of the catheter 15 has been inserted inside a ventricle, the catheter 15 is sequentially retracted with respect to the anchoring device 1. First the ventricular part 3 of the anchoring device 1 is fully released. In said first step, the ventricular part 3 expands immediately and adopts a first shape defining a mechanical stop 3*d*, as shown in FIG. 3A. The outer wall 4 of the ventricular part 3 indeed (i) protrudes with respect to the catheter 15 or to the extraventricular part 2 and (ii) presents proximally an angle of about 90° with respect to the longitudinal axis of the anchoring device 1. The external diameter of the mechanical stop 3*d* is preferably higher than the internal diameter of the native heart valve, thus the surgeon may abut the proximal part of the ventricular part 3 against the sub-annular surface of the heart valve annulus thereby obtaining a mechanical feedback. Indeed the mechanical stop 3*d* of the ventricular part 3 defines an end-positon as the proximal side is adapted to abut against the sub-annular surface of the native annulus. Preferably the external diameter of the mechanical stop 3*d* ranges from 10 to 90 millimeters, preferably from 20 to 80 millimeters, more preferably from 30 to 70 millimeters. According to one embodiment, the external diameter of the mechanical stop 3*d* is 20% larger than the diameter of the annulus of the native valve to be replaced.

If the extraventricular part 2 comprises only a single flange 6 extending from the inner wall 5, after removing the ventricular part 3 from the catheter 15, said ventricular part 3 expands and adopts a first shape defining a mechanical stop. The outer wall 4 of the ventricular part 3 indeed (i) protrudes with respect to the catheter 15 or to the extraventricular part 2 and (ii) presents proximally an angle ranging from 20° to 80° with respect to the longitudinal axis of the anchoring device 1. The external diameter of the mechanical stop is preferably higher than the internal diameter of the native heart valve, thus the surgeon may abut the proximal part of the ventricular part 3 against the sub-annular surface of the heart valve annulus thereby obtaining a mechanical feedback. Indeed the mechanical stop of the ventricular part 3 defines an end-positon as the proximal side is adapted to abut against the sub-annular surface of the native annulus. Preferably the external diameter of the mechanical stop ranges from 10 to 90 millimeters, preferably from 20 to 80 millimeters, more preferably from 30 to 70 millimeters. Moreover, in this embodiment, as the rim of the outer wall 4 of the ventricular part 3 may displace longitudinally, when the surgeon abuts the proximal part of the ventricular part 3 against the sub-annular surface of the annulus, the outer wall 4 dampens the movement thereby obtaining a mechanical feedback.

Once the anchoring device 1 has been properly positioned (i.e. by proper positioning of the mechanical stop 3*d* against the sub-annular surface of the heart valve), the surgeon may release, in a second step, the outer wall 4 of the extraventricular part 2, as illustrated in FIG. 3B. In an embodiment, as disclosed hereabove, the inner wall 5 of the extraventricular part 2 has a height higher than the height of the outer wall 4 of the extraventricular part 2. Said height difference allows a sequential release—upon gradual retraction of the catheter sheath with regard to the anchoring device 1—of, first, the outer wall 4 of the extraventricular part 2 and, then, the inner wall 5 of the extraventricular part 2. In another embodiment, as disclosed hereabove, the inner wall 5 and the outer wall 4 of the extraventricular part 2 have the same height. In said event the catheter 15 allows a sequential release of, first, the outer wall 4 of the extraventricular part 2 and, then, the inner wall 5 of the extraventricular part 2 through any means that one with ordinary skill in the art would find suitable. In another embodiment, the outer wall 4 of the extraventricular part 2 has a height higher than the height of the inner wall 5 of the extraventricular part 2.

At the stage shown in FIG. 3B, the surgeon may check the proper anchoring and the error-free functioning of the anchoring device 1. Said check may rely on the positioning and the validation provided by medical imaging. At the stage shown in FIG. 3B, the native annulus is pinched and pressed by the outer wall 4 of the anchoring device 1.

Once the surgeon has checked the proper sealing and the error-free functioning of the anchoring device 1, the surgeon may release, in a third step, the inner wall 5 of the extraventricular part 2, as illustrated in FIG. 3C.

After the release of the inner wall 5 of the extraventricular part 2, the surgeon may, if the anchoring device 1 comprises a prosthetic heart valve 13 mounted on a prosthetic heart valve support 12, check for the proper functioning of said prosthetic heart valve 13. Once the surgeon has checked the proper functioning of the prosthetic heart valve 13, he may release from the catheter the tie 10 linking the anchoring device 1 to the catheter 15.

According to an alternative embodiment, wherein the extraventricular part 2 does not comprise an outer wall 4, once the surgeon has released the ventricular part 3 and checked the proper sealing and the error-free functioning of the anchoring device 1, the surgeon may release the extraventricular part 2.

The anchoring device 1 of the present invention provides at a first step of the deployment, after release of the ventricular part 3 out of a catheter 15, a mechanical stop 3*d* which protrudes radially with respect to the catheter and presents an angle of about 90° with respect to the longitudinal axis of the anchoring device. In the event of the deployment inside a human body, said mechanical stop 3*d* allows optimal positioning of the device 1 with respect to the native heart valve. In a second step, after release out of the catheter 15 of the outer wall 4 of the extraventricular part 2 said mechanical stop 3*d* returns to its original shape. In the event of the deployment inside a human body, said mechanical stop 3*d* matches the shape of the heart wall and provides optimal geometrical anchorage. In other words, in a first step the proximal part of the ventricular part 3 presents an angle of about 90° for preventing the crossing of the native heart valve and after release of the outer wall 4 of the extraventricular part 2, the proximal part of the ventricular part 3 presents an angle, with respect to the longitudinal axis and in the direction of the ventricular part, ranging from 20° to 80°, preferably from 30° to 60°, more preferably from 40 to 50° for matching with the distal part of the native heart valve. Thus the anchoring device of the present invention provides, during a first step of the implantation, a mechanical stop which, after a second step deforms for matching the heart walls. After the second step, the surgeon may check proper positioning and sealing of the anchoring device and take the decision of re-introducing the anchoring device 1 in the catheter 15. In a third step, the surgeon may release the inner wall 5 of the extraventricular part 2. After the third step the surgeon may check for the proper functioning of the prosthetic heart valve 13, if applicable; and then may release the tie 10 still connecting the anchoring device 1 and the catheter 15. In the second step, as depicted in FIG. 3B, the outer wall 4 adopts the expanded configuration with a V-shaped groove 8. After the surgeon positioned the anchoring device 1 with the mechanical stop 3*d* abutting against the sub-annular surface, the V-shape groove 8 enables self-positioning of the anchoring device 1 by centering the anchoring device 1 with respect to the heart valve apparatus and especially with respect to the annulus. Indeed, due to the V-shaped groove 8, the anchoring device 1 is (i) positioned in the plane of the native annulus, (ii) centered in the plane of the native annulus and also maintained in said plane, thereby preventing migration. The V-shaped groove 8 precisely maintains and contains the native annulus between the edges of the groove.

In an embodiment, the anchoring device 1 may be used for anchoring a prosthetic heart valve in a patient's heart by implementing the following steps:
- providing a catheter 15 comprising a crimped anchoring device 1, wherein the ventricular part 3 is located distally and the extraventricular part 2 is located proximally within said catheter 15;
- expanding the ventricular part 3 in the ventricle, so that the ventricular part 3 provides a mechanical stop 3d, which prevents crossing the native heart valve;
- positioning the anchoring device 1 in the patient's heart so that the proximal part of the mechanical stop 3d abuts over the distal surface of the patient's native heart valve; and
- expanding the extraventricular part 2 so that:
  - the extraventricular part 2 lies over a proximal surface of the patient's native heart valve;
  - the mechanical stop 3d deforms itself and fits with the distal surface of the patient's native heart valve; and
  - the V-shaped groove 8 contains the native annulus and centers the anchoring device 1 with respect to said annulus.

In an embodiment, the anchoring device 1 is expanded by self-expansion or by means of an expansion arrangement such as for example a balloon, as well known to those skilled in the art. However, when the anchoring device 1 comprises a prosthetic heart valve 13, the expansion is achieved only by self-expansion. In an embodiment, the anchoring device 1 may be oversized with respect to the patient's anatomy in order to ensure constant pressure and prevent slipping of the anchoring device 1 by applying additional stresses to the surrounding tissues.

Figures 4A, 4B, 4C:
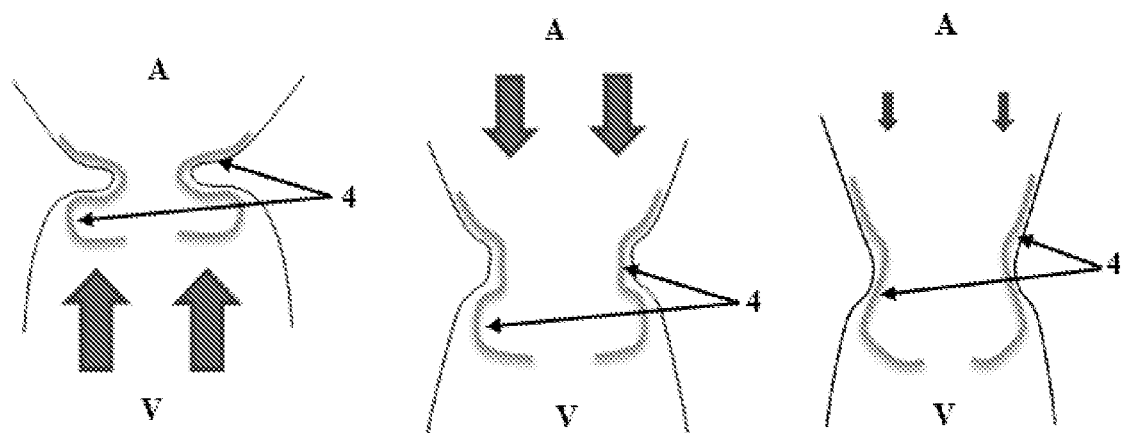
FIGS. 4A, 4B and 4C are sectional drawings of the outer wall of an anchoring device expanded at the level of a native heart valve, during a cardiac cycle, according to one embodiment of the present invention.

After full deployment of the anchoring device 1, geometrical anchorage is achieved. FIGS. 4A, 4B and 4C illustrate the geometrical anchorage of the anchoring device 1. The geometrical anchorage relies on a radial sealing (preventing paravalvular leakage) and on a longitudinal anchorage. As shown in FIGS. 4A, 4B and 4C, the anchoring device 1 prevents slipping with respect to the heart wall due to longitudinal anchorage on each side of the annulus, especially due to the V-shaped groove 8 and optionally the plurality of arms 16 and the grabbing mechanism.

In the event of dispositioning, prosthetic heart valve malfunction or paravalvular leak, the anchoring device 1 must be retrievable into the catheter 15.

In an embodiment wherein the outer wall 4 has not been deployed (i.e. before the second step), the anchoring device 1 is be re-introduced in the catheter 15 by traction of the device inside the catheter 15.

In an embodiment wherein the outer wall 4 has been deployed (i.e. after the second step) and wherein a tie 10 connects the catheter 15 to the outer wall 4 of the anchoring device 1, the anchoring device 1 may be re-introduced in the catheter 15 by traction on the tie 10. Said traction on the tie 10 affects the outer wall 4 of the extraventricular part 2 of the anchoring device 1 from an expanded state to a collapsed or crimped state, enabling re-introduction of the whole device inside the catheter 15.

In an embodiment, wherein the outer wall 4 has been deployed (i.e. after the second step) and wherein a tie 10 connects the catheter to the inner wall 5 of the anchoring device 1, re-introduction cannot be achieved as explained hereabove and must be achieved by turning the outer wall 4 inversely, as illustrated in FIG. 5.

Figure 5A:
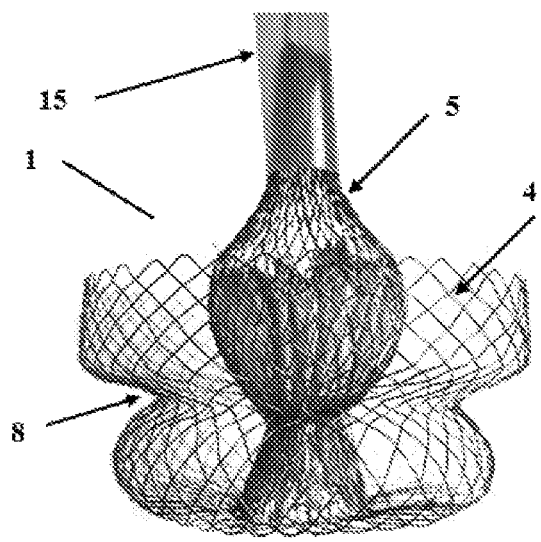
FIGS. 5A, 5B, 5C and 5D are side views of an anchoring device, according to one embodiment of the present invention, during the sequential re-introduction of the anchoring device inside a catheter.
Figure 5B:
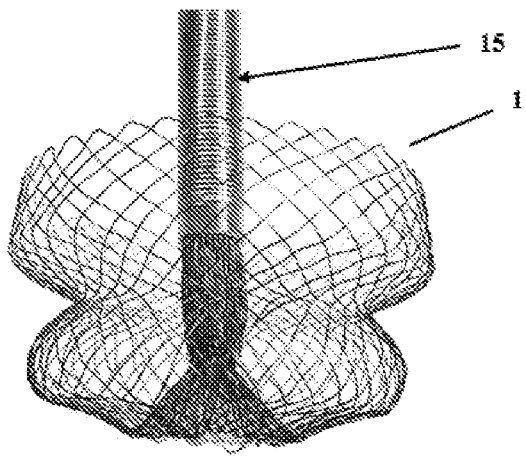
Figure 5C:
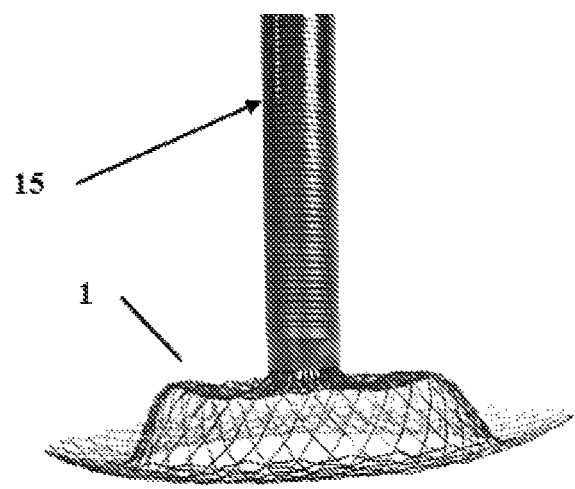
Figure 5D:
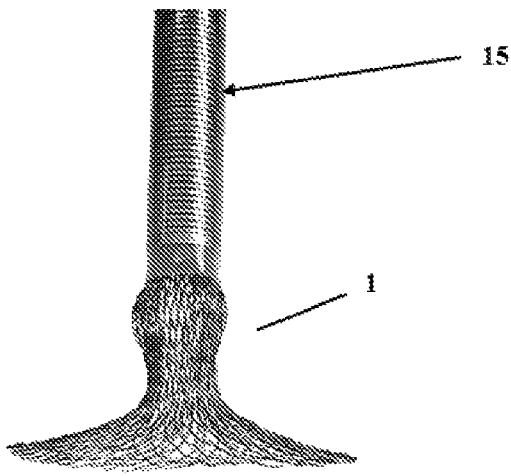

In FIG. 5A, the inner wall 5 of the extraventricular part 2 is located inside the catheter 15. Said embodiment may be achieved either after the second step of the deployment or after the third step of the deployment by traction on the tie 10 enabling (i) crimping of the inner wall 5 of the extraventricular part 2 of the anchoring device 1, and (ii) partial re-introduction of the inner wall 5 of the extraventricular part 2 of the anchoring device 1 in the catheter 15. By further traction on the proximal part of the anchoring device 1, the anchoring device 1 will be sequentially re-introduced inside the catheter 15: first the whole inner wall 5 of the extraventricular part 2 (cf. FIG. 5B), then the inner wall 5 of the ventricular part 3, the outer wall 4 of the ventricular part 3 (cf. FIG. 5C) and finally the outer wall 4 of the extraventricular part 2 (cf. FIG. 5D). During the retraction of the anchoring device 1 inside the catheter 15, the outer wall 4 turns inversely (i.e. folded into itself outwardly). In an embodiment, once the anchoring device 1 has been re-introduced inside the catheter 15, the anchoring device 1 may not be re-used.

Figure 9:
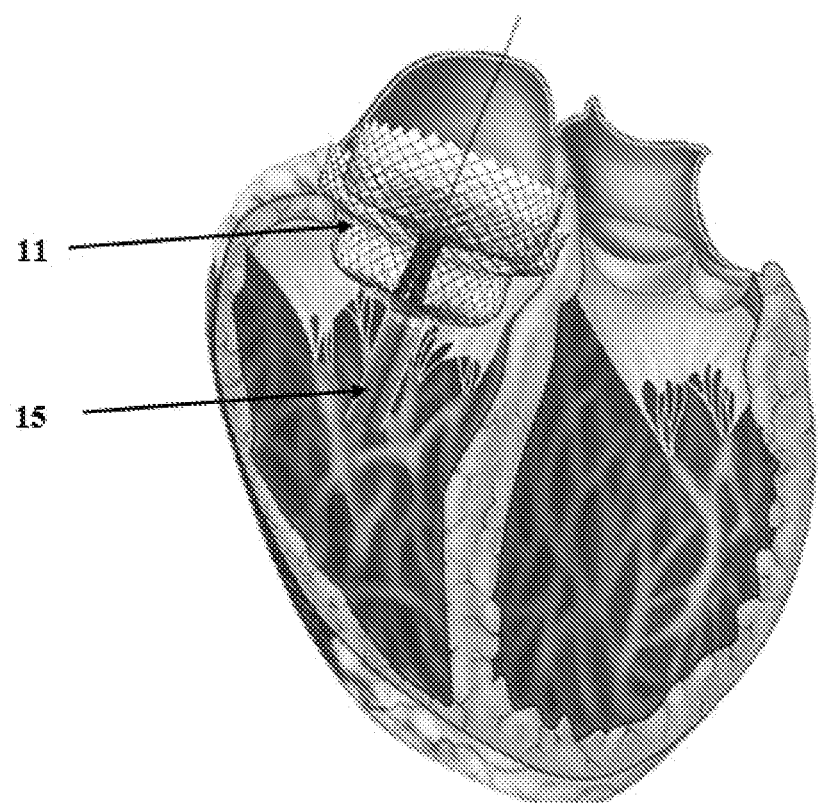
FIG. 9 is a sectional view, illustrating the positioning in a human heart of the anchoring system according to one embodiment of the present invention, wherein the deployment has been implemented sequentially with first release of the extraventricular part and then release of the ventricular part.

The following description is related to the deployment of the anchoring device 1 out of a catheter 15, wherein the distal end of the catheter 15 is located in an atrium or an artery before the beginning of the deployment (cf. FIG. 9). The extraventricular part 2 is thus located distally and the ventricular part 3 is located proximally within the lumen of the catheter 15. Said deployment is illustrated in FIGS. 6A, 6B, 6C and 6D.

Figure 6A:
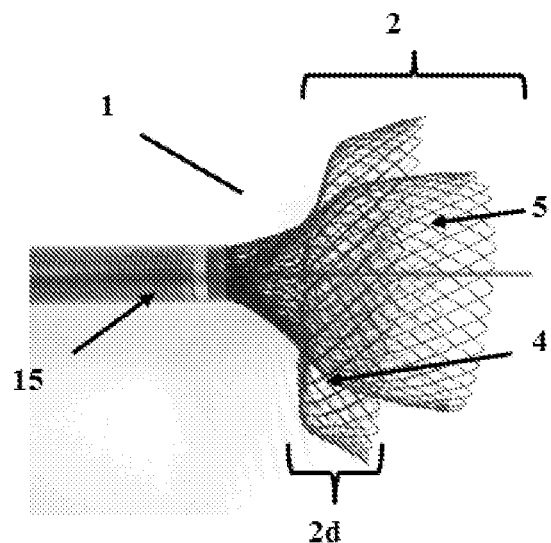
FIGS. 6A, 6B, 6C and 6D are side views of an anchoring device during deployment out of a catheter according to an embodiment of the present invention.

Once the distal end of the catheter 15 has been inserted inside an atrium or an artery, the catheter 15 is sequentially retracted with respect to the anchoring device 1. First the extraventricular part 2 (i.e. the cylindrical portion 7, if applicable, and the extraventricular flange(s) 6) of the anchoring device 1 is fully released. In said first step, the extraventricular flange 6 expands immediately and adopts a first shape defining a mechanical stop 2d, as shown in FIG. 6A. Said extraventricular flange 6 indeed (i) protrudes with respect to the catheter 15 or to the ventricular part 3 and (ii) presents proximally an angle of about 90° with respect to the longitudinal axis of the anchoring device 1. The external diameter of the mechanical stop is preferably higher than the internal diameter of the native heart valve, thus the surgeon may abut the proximal part of the extraventricular part 2 against the super-annular surface of the heart valve annulus thereby obtaining a mechanical feedback. Indeed the mechanical stop 2d of the extraventricular part 2 defines an end-positon as the proximal side is adapted to abut against the super-annular surface of the native annulus. Preferably the external diameter of the mechanical stop 2d ranges from 10 to 90 millimeters, preferably from 20 to 85 millimeters, more preferably from 30 to 70 millimeters.

Figure 6B:
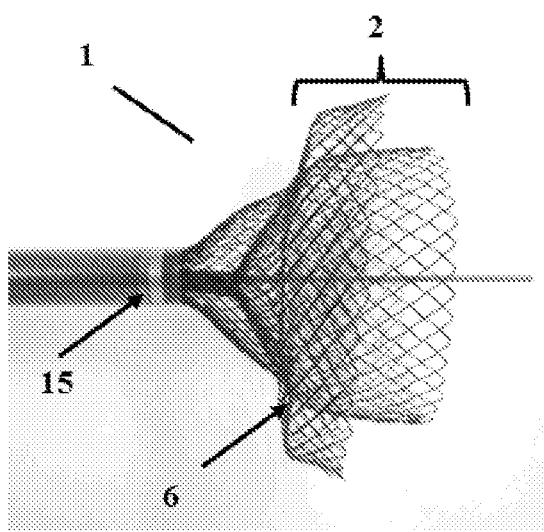
Figure 6C:
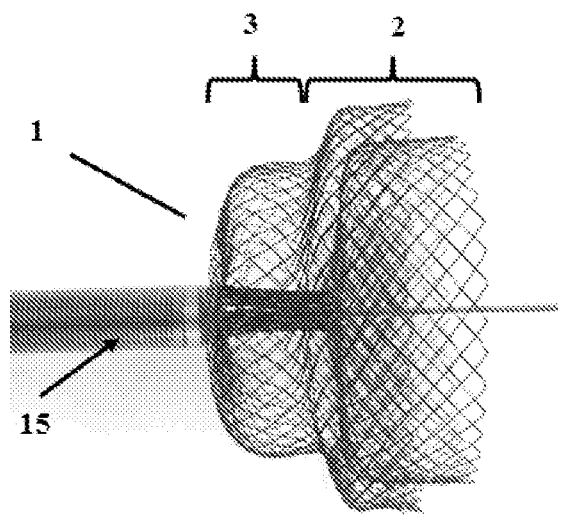

Once the anchoring device 1 has been properly positioned (i.e. by proper positioning of the mechanical stop 2d against the super-annular surface of the heart valve), the surgeon may release, in a second step, the outer wall 4 of the ventricular part 3, as illustrated in FIGS. 6B and 6C. At the stage shown in FIG. 6C, the surgeon may check the error-free functioning of the anchoring device 1. Said check may rely on the positioning and the validation provided by medical imaging. At the stage shown in FIG. 6C, the native annulus is pinched and pressed by the V-shaped groove 8 of the anchoring device 1.

Figure 6D:
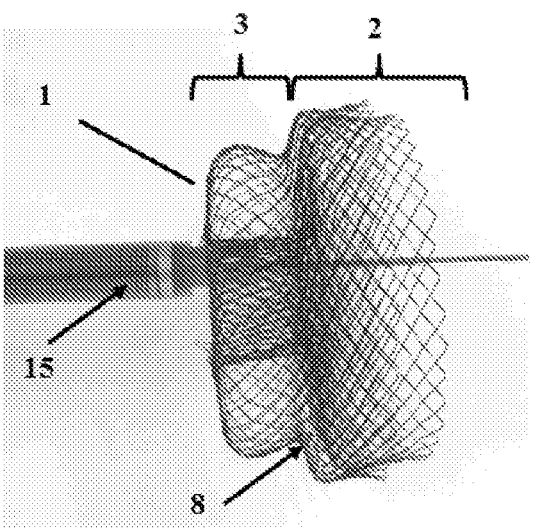

Once the surgeon has checked the error-free functioning of the anchoring device 1, the surgeon may release, in a third step, the inner wall 5 of the ventricular part 3, as illustrated in FIG. 6D.

After the release of the inner wall 5 of the ventricular part 3, the surgeon may, if the anchoring device 1 comprises a prosthetic heart valve 13 mounted on a prosthetic heart valve support 12, check for the proper functioning of said prosthetic heart valve 13.

The anchoring device 1 of the present invention provides at a first step of the implantation, after release of the extraventricular part 2, a mechanical stop 2d which protrudes radially with respect to the catheter 15 and presents an angle of about 90° with respect to the longitudinal axis of the anchoring device 1. In the event of the deployment inside a human body, said mechanical stop 2d allows optimal positioning of the device 1 with respect to the native heart valve. In a second step, after release of the outer wall 4 of the ventricular part 3 said mechanical stop 2d return to its original shape. In the event of deployment inside a human body, said mechanical stop 2d matches the shape of the heart wall and provides optimal geometrical anchorage. In other words, in a first step the proximal part of the extraventricular part 2 presents an angle of about 90° for preventing the crossing of the native heart valve and after release of the outer wall 4 of the ventricular part 3, the proximal part of the extraventricular part 2 presents an angle, with respect to the longitudinal axis and in the direction of the ventricular part, ranging from 65° to 110°, preferably from 75° to 100°, more preferably from 85° to 105° for matching with the distal part of the native heart valve. Thus the anchoring device of the present invention provides, during a first step of the implantation, a mechanical stop which, after a second step deforms for matching the heart walls. After the second step, the surgeon may check proper positioning and sealing of the anchoring device 1 and take the decision of re-introducing the anchoring device 1 in the catheter 15. In a third step, the surgeon may release the inner wall 5 of the ventricular part 3. After the third step the surgeon may check for the proper functioning of the prosthetic heart valve 13, if applicable. In the second step, as depicted in FIGS. 6C and 6D, the outer wall 4 adopts the expanded configuration with a V-shaped groove 8. After the surgeon positioned the anchoring device 1 with the mechanical stop 2d abutting against the super-annular surface, the V-shape groove 8 enables self-positioning of the anchoring device 1 by centering the anchoring device 1 with respect to the heart valve apparatus and especially with respect to the annulus. Indeed, due to the V-shaped groove 8, the native annulus is centered in the bottom of the groove, precisely maintaining and containing the native annulus between the edges of the groove.

In an embodiment, the anchoring device 1 may be used for anchoring a prosthetic heart valve in a patient's heart by implementing the following steps:
  providing a catheter 15 comprising a crimped anchoring device, wherein the extraventricular part 2 is located distally and the ventricular part 3 is located proximally within said catheter 15;
  expanding the extraventricular part 2 in an atrium or an artery, so that the extraventricular part 2 provides a mechanical stop 2d, which prevents crossing the native heart valve;
  positioning the anchoring device in the patient's heart so that the proximal part of the mechanical stop 2d abuts over the distal surface of the patient's native heart valve; and
  expanding the ventricular part 3 so that:
    the ventricular part 3 lies over a proximal surface of the patient's native heart valve;
    the mechanical stop 2d deforms itself and fits with the distal surface of the patient's native heart valve; and
    the V-shaped groove 8 contains the native annulus and centers the anchoring device 1 with respect to said annulus.

In an embodiment, the anchoring device 1 is expanded by self-expansion or by means of an expansion arrangement such as for example a balloon, as well known to those skilled in the art. In an embodiment, the anchoring device 1 may be oversized with respect to the patient's anatomy in order to ensure constant pressure and prevent slipping of the anchoring device 1 by applying additional stresses to the surrounding tissues. After full deployment of the anchoring device 1, geometrical anchorage is achieved as explained hereabove and as illustrated in FIGS. 4A, 4B and 4C.

In the event of mispositioning, prosthetic heart valve malfunction or paravalvular leak, the anchoring device 1 must be retractable into the catheter 15. Said re-introduction is achievable until the step illustrated in FIG. 6B, i.e. before the full deployment of the outer wall 4 of the ventricular part 3. In an embodiment wherein the outer wall 4 of the ventricular part 3 has not been fully deployed, the anchoring device 1 may be re-introduced in the catheter 15 by traction of the anchoring device 1 inside the catheter 15.

The present invention also relates to an anchoring system designed for implantation of a prosthetic heart valve in a mammalian heart.

In an embodiment, the anchoring system 11 comprises an anchoring device 1, a prosthetic heart valve support 12 and a prosthetic heart valve 13 mounted in the prosthetic heart valve support 12, preferably a prosthetic heart valve 13. In an alternative embodiment, the prosthetic heart valve is directly mounted in the anchoring device and the anchoring system does not comprise a prosthetic heart valve support.

In an embodiment, the prosthetic heart valve support 12 is designed for supporting the prosthetic heart valve 13. In an embodiment, the prosthetic heart valve support 12 has a circular cross-section with a diameter higher or equal to D4. In another embodiment, the prosthetic heart valve support 12 has a D-shape cross-section. In an embodiment, the prosthetic heart valve support 12 has a constant cross-section along its length. In another embodiment, the cross-section of the prosthetic heart valve support 12 differs along its length. In an embodiment, the length of the prosthetic heart valve support 12 ranges from 5 to 50 millimeters, preferably from 10 to 40 millimeters, more preferably from 15 to 35 millimeters. In an embodiment, the length of the prosthetic heart valve support 12 is equal or higher than the length of the prosthetic heart valve 13 intended to be inserted inside the prosthetic heart valve support 12. In an embodiment, the length of the prosthetic heart valve support 12 is lower, equal or larger than the height 113 of the ventricular part 3. In an embodiment, the prosthetic heart valve support 12 is adapted for minimizing turbulence in the blood flow.

In an embodiment, the prosthetic heart valve support 12 is made as a separate part with respect to the anchoring device 1. In another embodiment, the prosthetic heart valve support 12 is made in a single piece with the anchoring device 1 (i.e. with the inner wall 5 of the ventricular part 3). In another embodiment, the prosthetic heart valve 13 is directly attached to the anchoring device 1 without any prosthetic heart valve support 12. In a preferred embodiment, the prosthetic heart valve 13 is not mounted directly inside the inner wall 5. In an embodiment, the prosthetic heart valve support 12 is located inside the inner wall 5 of the ventricular part 3. In an embodiment, the prosthetic heart valve support 12 is solidarily attached to the anchoring device 1. In an embodiment, the prosthetic heart valve support 12 is solidarily attached to the inner wall 5 of the ventricular part 3. In an embodiment, the prosthetic heart valve support 12 is attached to the anchoring device 1 by any means that one of ordinary skill in the art would find suitable, such as for example suture, bonding, welding or mesh interlacing. In an embodiment, the prosthetic heart valve support 12 is linked to the to the inner wall 5 of the ventricular part 3 by any means that one of ordinary skill in the art would find suitable, such as for example suture, bonding, welding or mesh interlacing.

In an embodiment, the prosthetic heart valve support 12 is made of a mesh for ensuring attachment with the prosthetic heart valve 13. In an embodiment, said mesh is a flexible, compressible and expansible mesh. In an embodiment, the mesh of the prosthetic heart valve support 12 is a braided mesh or a continuous mesh obtained, for example, by laser cutting. In an embodiment, the mesh size is adapted for matching with the rim of the leaflets of the prosthetic heart valve 13. In an embodiment, the prosthetic heart valve 13 is attached to the prosthetic heart valve support 12 by any means that one of ordinary skill would find suitable, such as for example suture. In an embodiment, the prosthetic heart valve 13 is centered in the prosthetic heart valve support 12. In an embodiment, the prosthetic heart valve 13 is positioned completely inside the prosthetic heart valve support 12.

In an embodiment, the prosthetic heart valve support 12 is made from any material from any material that one skilled in the art would find suitable, such as any biocompatible material. In an embodiment, the prosthetic heart valve support 12 is made from any biocompatible alloy that one skilled in the art would find suitable such as for example a cobalt alloy, preferably a cobalt-chromium alloy; steel, preferably stainless steel; or a biocompatible shape memory alloy. In an embodiment, the prosthetic heart valve support 12 is made from a shape memory alloy, preferably Nitinol, allowing faster and easier deployment and return to its original expanded shape. In an embodiment, the transformation temperature of the shape memory alloy, preferably Nitinol, ranges from 0° C. to 50° C. In an embodiment, the transformation temperature of the shape memory alloy is about 37° C. In another embodiment, the transformation temperature of the shape memory alloy, preferably Nitinol, ranges from 0° C. to 20° C. in order to allow phase transformation immediately from the releasing of the prosthetic heart valve support 12.

In an embodiment, a cover 14 covers the prosthetic heart valve support 12 in order to prevent leaks between the prosthetic heart valve support 12 and the inner wall 5 of the anchoring device 1. In an embodiment, contacting the cover 14 of the prosthetic heart valve support 12 with the cover 9 of the anchoring device 1 prevents paravalvular or paraprosthetic leaks. In an embodiment, a cover 14 internally or externally covers the prosthetic heart valve support 12. In an embodiment, said cover 14 partially or totally covers the prosthetic heart valve support 12. In an embodiment, the cover 14 internally covers the prosthetic heart valve support 12 from 1 to 15 millimeters, preferably from 2 to 10 millimeters, below the distal end of the prosthetic heart valve 14. In an embodiment, the cover 14 internally covers the prosthetic heart valve support 12 from 1 to 15 millimeters, preferably from 2 to 10 millimeters, above the proximal end of the prosthetic heart valve 14. In an embodiment, the cover 14 comprises two covers internally covering the prosthetic heart valve support 12 from 1 to 15 millimeters, preferably from 2 to 10 millimeters, on each side of the prosthetic heart valve 13.

Figure 7A:
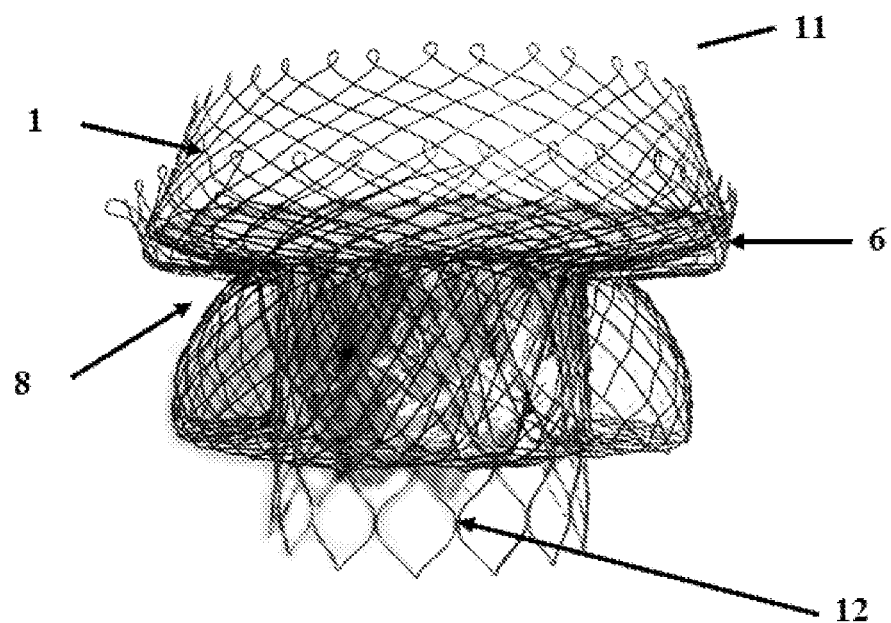
FIG. 7A is a side view of an anchoring system according to an embodiment of the present invention.

FIG. 7A illustrates a cross-sectional view of the anchoring system 11 comprising the anchoring device 1, the prosthetic heart valve support 12 and the prosthetic heart valve 13. As shown, the prosthetic heart valve support 12 may extend beyond the anchoring device 1.

Figure 7B:
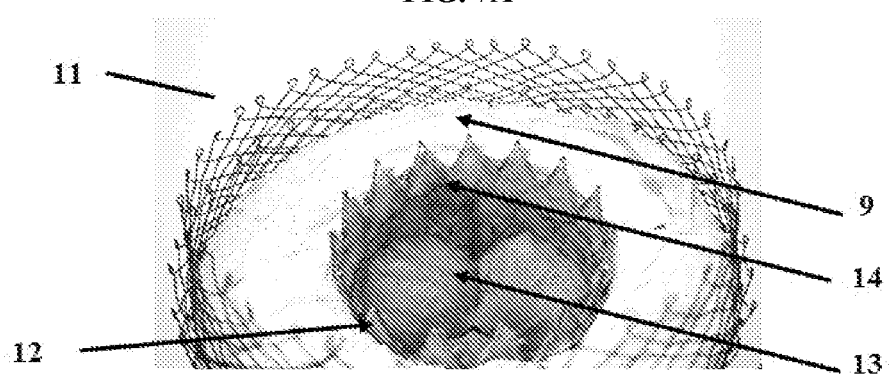
FIG. 7B is a top perspective view of an anchoring system according to an embodiment of the present invention.

FIG. 7B illustrates a top perspective view of the anchoring system 11. As shown, the anchoring system 11 comprises two covers (9 and 14), a prosthetic heart valve support 12 and a prosthetic heart valve 13. As shown, the prosthetic heart valve support 12 may extend beyond the extraventricular flanges 6 of the anchoring device 1 and the cover 14 may covers the prosthetic heart valve support 12 above the prosthetic heart valve 13.

Figure 7C:
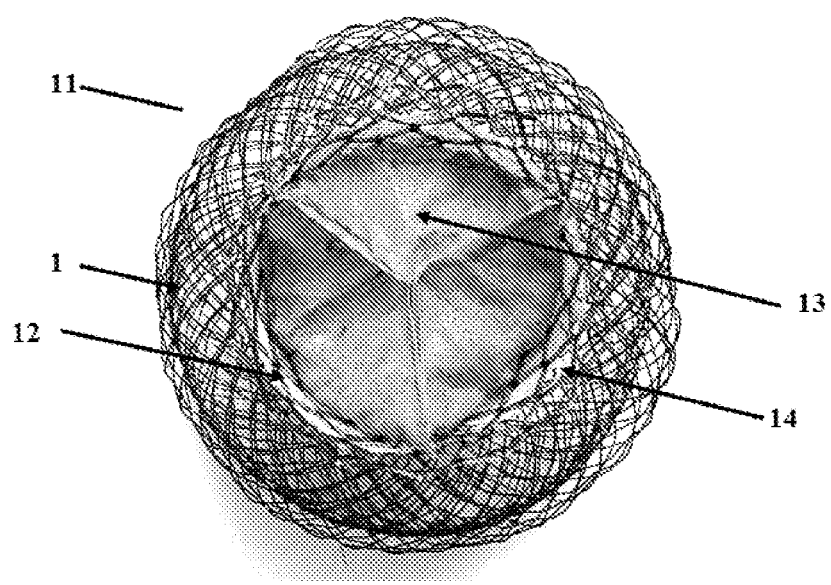
FIG. 7C is a bottom view of an anchoring system according to an embodiment of the present invention.

FIG. 7C illustrates a bottom perspective view of the anchoring system 11. As shown, the anchoring system 11 comprises the anchoring device 1, a prosthetic heart valve support 12, a prosthetic heart valve 13 and a cover 14. As shown, the prosthetic heart valve support 12 may extend beyond the anchoring device 1 and the cover 14 may covers the prosthetic heart valve support 12 below the prosthetic heart valve 13.

In an embodiment, the cover of the prosthetic heart valve support 12 or the cover of the anchoring device 9 are preferably a film or a fabric, preferably a biocompatible and nonthrombogenic film or fabric. In an embodiment, the cover of the prosthetic heart valve support 12 or the cover of the anchoring device 9 may be any biological (such as animal tissue) or synthetic material that one skilled in the art would find suitable. In an embodiment, the cover of the prosthetic heart valve support 12 or the cover of the anchoring device 9 are made from silicone, polytetrafluoroethylene, polyurethane, polyamide, polyester or mixture thereof. In an embodiment, the cover of the prosthetic heart valve support 12 or the cover of the anchoring device 9 may present natural resorption in the human body thus allowing anchorage by human cells after implantation. In an embodiment, the cover of the prosthetic heart valve support 12 or the cover of the anchoring device 9 are designed so that to allow optimal crimping and release of the anchoring device 1. In one embodiment, the cover of the prosthetic heart valve support 12 and the cover of the anchoring device 9 are made from the same or different materials.

In an embodiment, the prosthetic heart valve support 12 presents high stiffness. In an embodiment, the stiffness of the prosthetic heart valve support 12 is higher than the stiffness of the anchoring device 1. In an embodiment, the outer wall 4 has a lower stiffness than the inner wall 5 linked to the prosthetic heart valve support 12. Optimal functioning (i.e. proper opening and closing of the leaflets over years) of the prosthetic heart valve 13 requires a substantially symmetric and cylindrical support around the prosthetic heart valve 13. Thus the prosthetic heart valve support 12 is designed so that the cross-sectional shape remains stable during each cardiac cycle. In an embodiment, the outer wall 4 is mechanically isolated from the prosthetic heart valve support 12 such that the cross-sectional shape of the prosthetic heart valve support 12 remains stable and the prosthetic heart valve 13 remains competent when the anchoring device 1 is deformed in a non-circular shape in use, after implantation. The anchoring device 1 and the anchoring system 11 effectively absorb the distorting forces applied by the patient's anatomy. The anchoring system 11 has the structural strength integrity necessary to withstand the dynamic conditions of the heart over time, thus permanently anchoring a replacement heart valve and making it possible for the patient to resume substantially normal life.

In an embodiment, the anchoring system 11 and device 1 enable a percutaneous approach using a catheter 15 delivered through a vein or an artery into the heart or through the apex of the heart. Additionally, the embodiments of the system 11 and device 1 as described herein can be combined with many known surgeries and procedures. In an embodiment, the anchoring system 11 of the present invention is to be used for patients suffering from tricuspid insufficiency, mitral insufficiency, aortic valve insufficiency, pulmonary valve insufficiency, tricuspid stenosis, mitral stenosis, aortic valve stenosis or pulmonary valve stenosis.

The release and/or re-introduction of the anchoring device 1 out of and/or in the catheter 15 as disclosed in the detailed description hereabove is similar to the release and/or re-introduction of the anchoring system 11 comprising the anchoring device 1, the prosthetic heart valve support 12 and the prosthetic heart valve 13, as a person skilled in the art can easily understand. In an embodiment, the deployment or release of the anchoring device 1 is concomitant with the deployment or release of the prosthetic heart valve 13.

Figure 13:
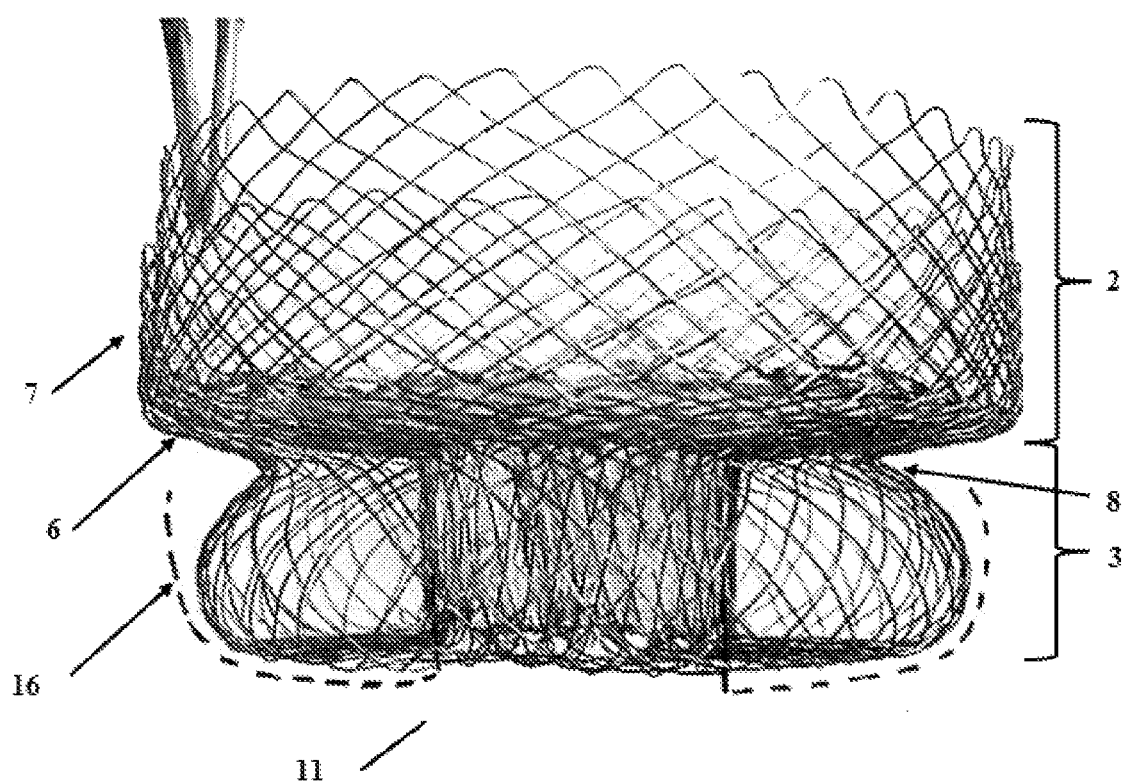
FIG. 13 is a side view of an anchoring system according to an embodiment of the present invention wherein the anchoring system comprises a plurality of arms extending outwardly from the prosthetic heart valve support.

According to one embodiment, as depicted in FIG. 13, the anchoring system 11 further comprises a plurality of arms 16 for securing the system with respect to the native heart valve. The plurality of arms 16 extends outwardly from the prosthetic heart valve support 12. According to one embodiment, the plurality of arms extends outwardly from the ventricular end of the prosthetic heart valve support 12 in the direction of the extraventricular part 2. Said plurality of arms 16 are configured to be size and shape for providing a positioning and anchoring function when the anchoring system 11 is deployed at the native heart valve location.

In one embodiment, the plurality of arms 16 has a length sufficient to extend completely into engagement with the annulus tissue behind the leaflets. In another embodiment, the plurality of arms has a shorter length for remaining on the inner sides of the leaflets. According to one embodiment, the plurality of arms 16 comprises arms with different length and modes of engagement with the leaflets or other native tissue.

The plurality of arms 16 may alternatively be configured to engage or couple to the chordae, papillary muscles or ventricular walls to enhance anchoring. In one embodiment, each arms of the plurality of arms 16 have independent lengths. In one embodiment, the native leaflets are pinched or sandwiched between the plurality of arms 16 and the outer wall 4.

According to one embodiment, the plurality of arms 16 is formed integrally with the prosthetic heart valve support 12. According to another embodiment, the plurality of arms 16 is separate component that are attached to the prosthetic heart valve support 12. According to one embodiment, the plurality of arms 16 is made from the same material than the prosthetic heart valve support 12 of the anchoring system 11.

The present invention also relates to a kit for performing heart valve replacement comprising an anchoring device 1, a prosthetic heart valve support 12, a prosthetic heart valve 13 connected to said prosthetic heart valve support 12, and optionally a catheter 15.

What is claimed is:

1. A method of treating heart valve disease comprising:
   providing an anchoring system for positioning a prosthetic heart valve inside a heart, the system comprising an expandable anchoring device, a prosthetic heart valve support, and a prosthetic heart valve mounted in the prosthetic heart valve support, wherein the anchoring device comprises a groove for accommodating the native valve;
   positioning the system such that the groove resides between the ventricle and the atrium or artery;
   wherein the groove is between a ventricular part and an extraventricular part of the anchoring device;
   wherein the ventricular part includes a double wall; and
   wherein the anchoring device includes a plurality of arms extending outwardly from the outer wall of the ventricular part.

2. The method of claim 1, wherein contact between a bottom of the groove and an annulus is avoided.

3. The method of claim 1, wherein the groove allows the anchoring device to be self-positioning.

4. The method of claim 1, wherein the prosthetic heart valve is a tricuspid heart valve.

5. The method of claim 1, wherein the method includes a step of anchoring the anchoring system to the native heart tissue.

6. The method of claim 1, wherein the groove is a V-shaped groove.

7. The method of claim 1, wherein the groove has a depth of 5 to 15 mm.

8. The method of claim 1, wherein the groove is defined by two inclined walls.

9. The method of claim 1, wherein the anchoring device is configured to pinch sub- and supra-annular surfaces of an annulus without applying radial force on the annulus.

10. The method of claim 1, wherein the anchoring device is compressible and the method includes crimping the anchoring device into a radially collapsed configuration.

11. The method of claim 10, wherein the method includes introducing the crimped anchoring device into a lumen of a catheter.

12. The method of claim 11, wherein the method includes delivering the crimped anchoring device in the radially collapsed configuration with the catheter.

13. The method of claim 12, wherein the method includes deploying the anchoring device from the catheter.

14. The method of claim 13, wherein the deploying includes radially expanding the crimped anchoring device.

15. The method of claim 14, wherein the anchoring device is folded into itself before or after the step of delivering the anchoring device.

16. The method of claim 14, wherein the anchoring device comprises, before use, an outer wall and an inner wall connected at a folded end.

17. The method of claim 14, wherein the method includes advancing a distal end of the catheter until the distal end crosses a targeted native heart valve.

18. The method of claim 17, wherein the method includes one or any combination of:
   i) after the distal end of the catheter has been inserted inside the ventricle, sequentially retracting the catheter with respect to the anchoring device;
   ii) releasing the ventricular part of the anchoring device;
   iii) expanding the ventricular part to adopt a first shape defining a mechanical stop, wherein an outer wall of the ventricular part protrudes with respect to the catheter or to the extraventricular part, and the outer wall of the ventricular part presents proximally an angle of about 90° with respect to a longitudinal axis of the anchoring device;

iv) abutting a proximal part of the ventricular part against a sub-annular surface of a native annulus;

v) releasing an outer wall of the extraventricular part; or vi) releasing an inner wall of the extraventricular part.

19. The method of claim 18, wherein the method includes releasing the ventricular part, releasing the outer wall of the extraventricular part, and releasing the inner wall of the extraventricular part as three separate sequential steps.

20. The method of claim 1, wherein
the double wall includes spaced apart outer and inner walls connected at a folded end.

21. The method of claim 20, wherein the plurality of arms extend from a folded end of the double wall and the plurality of arms includes arms having different lengths.

22. The method of claim 20,
wherein D2 is a diameter of the extraventricular part of the anchoring device, D3 is a largest diameter of the ventricular part of the anchoring device, D4 is an internal diameter of the ventricular part, D5 is a smallest external diameter of the ventricular part, H1 is a height of the anchoring device, H2 is a height of the extraventricular part, and H3 is a height of the ventricular part;

wherein D2 is from 10 to 90 millimeters, D3 is from 10 to 90 millimeters, D4 is from 5 to 40 millimeters, D5 is from 10 to 75 millimeters, H1 is from 5 to 50 millimeters, H2 is from 1 to 20 millimeters, and H3 is from 1 to 45 millimeters.

23. The method of claim 22, wherein D2 is from 30 to 70 millimeters, D3 is from 30 to 70 millimeters and is higher than D2, D4 is from 15 to 25 millimeters, D5 is from 30 to 65 millimeters, H2 is from 5 to 10 millimeters, and H3 is from 10 to 25 millimeters.

24. The method of claim 20, wherein the inner wall is cylindrical and the outer wall is conical, wherein a smaller diameter of the conical outer wall is in a direction of the extraventricular part and a larger diameter of the conical outer wall is connected to the cylindrical inner wall at the folded end.

* * * * *